United States Patent
Van Cleve et al.

(10) Patent No.: US 6,327,915 B1
(45) Date of Patent: Dec. 11, 2001

(54) STRAIGHT TUBE CORIOLIS FLOWMETER

(75) Inventors: Craig Brainerd Van Cleve, Lyons; Charles Paul Stack, Louisville; Gregory Treat Lanham, Longmont, all of CO (US)

(73) Assignee: Micro Motion, Inc., Boulder, CO (US)

( * ) Notice: Subject to any disclaimer, the term of this patent is extended or adjusted under 35 U.S.C. 154(b) by 0 days.

(21) Appl. No.: 09/343,836

(22) Filed: Jun. 30, 1999

(51) Int. Cl.[7] .................................................. G01F 1/84
(52) U.S. Cl. ........................................... 73/861.357
(58) Field of Search ........................ 73/861.01, 861.08, 73/861.18, 861.19, 861.354, 861.355, 861.357

(56) References Cited

U.S. PATENT DOCUMENTS

| | | |
|---|---|---|
| 4,768,384 | 9/1988 | Flecken et al. . |
| 4,876,879 * | 10/1989 | Ruesch .................................. 73/32 A |
| 5,027,662 * | 7/1991 | Titlow et al. .................... 73/861.356 |
| 5,365,794 | 11/1994 | Hussain et al. . |
| 5,381,697 | 1/1995 | Van der Pol . |
| 5,473,949 * | 12/1995 | Cage et al. ...................... 73/861.356 |
| 5,497,665 * | 3/1996 | Cage et al. ...................... 73/861.356 |
| 5,691,485 | 11/1997 | Endo et al. . |
| 5,753,827 * | 5/1998 | Cage .................................. 73/861.356 |
| 5,827,979 | 10/1998 | Schott et al. . |

FOREIGN PATENT DOCUMENTS

| | | |
|---|---|---|
| 4224379 C1 | 12/1993 | (DE) . |
| 0 759 541 A1 | 2/1997 | (EP) . |
| 0 759 542 A1 | 2/1997 | (EP) . |
| 0578113 B1 | 11/1997 | (EP) . |

* cited by examiner

*Primary Examiner*—Max Noori
(74) *Attorney, Agent, or Firm*—Chrisman, Bynum & Johnson P. C.

(57) ABSTRACT

Method and apparatus for providing compensation of mass flow rate and density for the flow tube of a single straight flow tube Coriolis flowmeter. Thermal stress compensation is provided by the use of a plurality of sensors on various portions of the flowmeter. A first sensor is coupled to the flow tube and provides information regarding the flow tube temperature. A plurality of additional sensors are connected to form a network having a two wire output. The additional sensors apply a composite signal over the two wire output of the network to meter electronics. The network signal represents the composite temperature of the flowmeter elements that can cause thermal stress on the flow tube when a temperature differential exists between the flow tube and the temperature of these plurality of elements. The additional elements include the balance bar and the flowmeter case. Sensitivity compensation is provided by the use of a novel algorithm. Density is measured in a single tube flowmeter that is calibrated using two materials of different densities by the use of density equation that has non linear components representing the deviation of the meter calibration from linear.

75 Claims, 7 Drawing Sheets

STRAIGHT TUBE CORIOLIS FLOWMETER

FIELD OF THE INVENTION

This invention relates to a method and apparatus for providing mass flow and density compensation, as well as a density determination in a straight tube Coriolis flowmeter.

PROBLEM

All Coriolis flowmeters require compensation to correct signals generated by the Coriolis force induced displacement of the vibrating flow tube. These signals represent the phase difference between the spaced apart flow tube pick offs and are indicative of the material flow through the flowmeter. Curved and straight tube meters both need compensation for the change in elastic modulus of the flow tube with temperature. As the flow tube temperature rises, the modulus decreases and the meter becomes more sensitive. Compensation for the change in the elastic modulus is easily achieved by use of a temperature sensor on the flow tube and the appropriate compensation algorithm in the meter electronics.

Straight tube meters have an additional problem in that the flow tube can be put in tension or compression by unequal amounts of thermal expansion or contraction of the various components of the flowmeter. Tension on the flow tube makes it less sensitive to the Coriolis force while compression makes it more sensitive. Typically thermal stress compensation has been attempted using two temperature sensors; one on the flow tube and one on the case or balance bar. The problem with the use of two temperatures sensors is that there are at least three major components which can have an impact on the thermal stress of the flow tube. If the second sensor is on the case, then the impact of the balance bar's temperature is not taken into account. Likewise if the second sensor is on the balance bar, then the case temperature is not taken into account.

The use of three independent temperature sensors would be an improvement over two temperature sensors, however, three independent sensors would require three pairs of wires from the sensor to the meter electronics. Extra wires can be expensive if the meter electronics is far from the sensor. Furthermore, compensation algorithms would be required to apply the appropriate weighting factors to the various temperatures, since the case temperature does not have the same effect on the flow sensitivity as the balance bar temperature.

U.S. Pat. No. 4,768,384 to Flecken et al. discloses a straight tube Coriolis flowmeter which provides thermal stress compensation by the use of sensors that measure the flow tube temperature, and the case temperature. A correction circuit receives the pick off signals and generates a corrected output signal that eliminates the affect of stress and temperature on the measurement result. The Flecken et al. flowmeter operates satisfactorily to provide compensation for the change in elastic modulus of the flow tube. The reason is that this compensation requires nothing more than a determination of the flow tube temperature and an appropriate correction based upon known relationships between temperature, elastic modulus, and meter sensitivity.

The Flecken flowmeter can also determine the temperature differential between the flow tube and the case and make a stress correction of the pick off signal information. However, an assumption must be made by Flecken about the temperature of the balance bar. In a thermal steady state condition, the flowing material temperature and the ambient temperature are assumed to have been constant for a long period of time. Under this condition, the balance bar and the flow tube achieve essentially the same temperature as the flowing material temperature. In the thermal transient condition, the flowing material has a sudden change in temperature, such as when the flow is first started. Under this condition, initially, the balance bar and the case are likely to have the same temperature as the environment. The flow tube has the same temperature as the flowing material. In general, flowmeters experience both thermal transient and steady state conditions. The balance bar temperature starts at the ambient temperature and slowly changes to the temperature of the flowing material.

The compensation algorithm of the Flecken flowmeter must make an assumption regarding the balance bar temperature since its two temperature sensors are on the flow tube and the case. It therefore cannot distinguish between steady state and transient conditions of the balance bar temperature. This is a problem since the two conditions produce different stress in the flow tube and different sensitivity of the flowmeter. In the transient condition where the balance bar is initially at the case temperature, both the case and the balance bar apply force to the flow tube. In the steady state condition where the balance bar temperature is nearly equal to the flow tube temperature, the balance bar helps the flow tube resist the force applied by the case. The flow tube therefore experiences a higher stress in the thermal transient condition than in the thermal steady state condition. The best that the compensation of Flecken can do is assume the balance bar temperature to be between the flow tube and case temperatures and suffer inaccuracies at either the transient or steady state extremes.

Another prior art attempt to provide thermal stress compensation for a Coriolis flowmeter is seen in U.S. Pat. No. 5,476,013 to Hussain et al. It provides some thermal stress compensation by using parts that have the same coefficient of expansion. This eliminates thermal stresses when all of the elements are at the same temperature, but it does not address the common situation in which the different components have different temperatures. U.S. Pat. No. 5,381,697 to Van der Pol discloses a Coriolis flowmeter in which thermal stress compensation is provided, in a first embodiment, using two temperature sensors for measuring the temperature of the flow tube. A second embodiment uses a temperature sensor on the flow tube along with a length change sensor on the flow tube. This could, in theory, provide accurate thermal stress compensation. It has a problem, however, in that the means of measuring the length change in the flow tube are not as simple or reliable as temperature sensors.

In addition to the flow measurement, the density measurement of straight tube meters is also degraded by thermal stress. Coriolis flowmeters are known for providing accurate density measurements of the flowing material. Density is determined from the resonant frequency at which the flow tube is vibrated. In curved tube meters, the resonant frequency must be corrected for the change in the tube's elastic modulus with temperature. Also, a correction has to be made for the slight decrease in resonant frequency with mass flow rate as shown in U.S. Pat. No. 5,295,084. Straight tube meters require, in addition, compensation for thermal stress of the flow tube. The flow tube resonant frequency rises as it is tensioned and falls when it is compressed, like a guitar string. If these frequency changes are not compensated, a flow tube in tension will give an erroneously low reading for density and a flow tube in compression will give an erroneously high density reading. The deficiencies of the prior art meters in determining the thermal stress in the flow tube thus lead to inaccuracies in the density measurement.

Single tube straight tube meters have another problem in density measurement that dual tube meters do not have. When material density changes in a dual tube meter, the mass of the fluid in each flow tube changes by the same amount so that the vibrating masses remain in balance without involving any mass besides the material filled flow tubes. When the material density changes in a single straight tube meter, the mass of the flow tube changes while the mass of the balance bar remains unchanged. As a result of this mass imbalance, the location of the vibration nodes change. The vibration nodes are the stationary regions between the flow tube and balance bar that do not vibrate with either member. The vibration nodes move toward the balance bar when the material density decreases and toward the flow tube when the material density increases. With a material density increase, flow meter elements near the nodal regions that had been vibrating with the flow tube would end up vibrating with the balance bar. The movement of the nodal region towards the flow tube transfers mass from the heavy member to the light member. This is an effective way to maintain meter balance, but it creates a problem in density measurement.

In dual tube meters density calibration is done by measuring the tube vibration period of vibration (the inverse of frequency) with air and with water. The tube vibration period squared is proportional to the material density. Thus a graph of tube vibration period squared versus density yields a straight line. This line can then be used to interpolate or extrapolate for other measured tube vibration periods (corrected for temperature and stress) to determine the density of the material. Of course, the straight line and the interpolation are all done mathematically in the meter electronics.

For single tube meters the graph of tube vibration period squared versus material density is not a straight line because of the mass transfer with the shift of the nodal regions. When the material density increases, the nodal shift transfers some of the increased mass to the balance bar so that the tube vibration period does not increase as much as it would for a dual tube meter. Likewise, when the material density decreases, the nodal shift transfers some of the mass from the balance bar to the flow tube so that it does not decrease as much as it would for a dual tube meter. The result of this mass transfer is that the method of using the straight line determined by air and water density for calibrations leads to errors in the density output of the meter. A three point density calibration using materials having densities from 0.8 to 1.2 gm/cc gives an accurate curve from which to interpolate densities, but the expense and difficulty of using three different density materials is considerable.

It can therefore be seen that compensation for a straight tube flowmeter cannot provide accurate flow and density information if it does not provide accurate thermal information concerning all the major components of the flowmeter. It also cannot provide accurate density information if it does not take into account the non-linearity of the density versus tube vibration period squared relationship.

SOLUTION

The above problems are solved and an advance in the art is achieved by the method and apparatus of the invention which provides thermal stress compensation for a straight tube Coriolis flowmeter. The present invention overcomes these problems by the use of a single temperature sensor on the flow tube, as in prior art meters, and a network of temperature sensors on other parts of the meter. The flow tube sensor serves two functions. One function is to provide the temperature used to compensate for the change in stiffness (elastic modulus) of the flow tube with temperature. The other function is to provide a reference temperature for the calculation of thermal stress so as to compensate for its effect on flow sensitivity and density.

The thermal stress compensation of the invention functions in conjunction with velocity sensors (pick offs) affixed to the flowmeter flow tube. The flow tube is vibrated at its resonant frequency during conditions of material flow. This induces Coriolis deflections in the flow tube that are detected by pick offs affixed to different portions of the flow tube. The phase difference between the signal outputs of the two pick offs is proportional to the material mass flow rate. The resonant frequency is inversely proportional to the square root of the material density. The pick off phase delay and resonant frequency are applied to meter electronic circuitry which processes the signals to generate the mass flow rate and density. However, it is necessary that the meter electronics compensate the flowmeter's proportionality constants for flow rate and density to provide a correction for the thermal state, material density, and flow rate of the flowmeter.

The method and apparatus of invention minimizes problems caused by temperature differentials between the various parts of a Coriolis flowmeter. The present invention provides thermal compensation for changes in the elastic modulus of the oscillating system of the flowmeter. It further provides thermal stress compensation for temperature differentials between the elements of a flowmeter. These elements primarily comprise a flow tube, a balance bar and a case.

The method and apparatus of the present invention achieves thermal stress compensation of output data by providing a plurality of sensors on the various parts of the flowmeter to detect temperature differentials, both steady state and transient, between the flow tube, the balance bar and the flowmeter case. The invention provides at least one temperature sensor on the flow tube and further provides at least one sensor on the case as well as a plurality of sensors on the balance bar. In another embodiment of the invention, other sensors may be provided on other flowmeter parts including on a case connect link and/or on a case end element of the flowmeter.

In accordance with the invention, a temperature sensor on the flow tube is connected by a pair of wires to the meter electronics to provide flow tube temperature information. The other sensors, including those on the balance bar and on the case, are connected in a network. The network is also connected by a pair of wires to the meter electronics. The temperature sensors on the flow tube and in the network can be RTDs, which are resistors that increase resistance with temperature. The meter electronics applies a voltage to the tube RTD via one of its two wires while the other wire serves as a return or ground wire. Likewise, the RTD network is supplied with voltage from the meter electronics via one of its two wires while the other is the RTD network's return or ground wire. The ground wire of the flow tube temperature sensor and the ground wire of the network of sensors can be combined at the flowmeter so that only three wires are needed to transmit temperature information to the meter electronics. The resistance of the flow tube sensor and the resistance of the sensor network are determined in the electronics from the current in each circuit and Ohm's law.

In one embodiment of the invention, one sensor is mounted on the flow tube as in prior art. In addition, a sensor is mounted on the case wall, another sensor is on the end of the balance bar and still another sensor is on the middle of the balance bar. These three sensors (excluding the one on the flow tube) are connected in series to form a network having a two wire output which is connected to the meter electronics. The three sensors comprising this network provide information to the meter electronics representing temperature conditions within the flowmeter that can cause stresses on the flow tube. Because they are connected in series, they provide the sum of the sensor temperatures in the network. The series network of sensors does not provide information to the meter electronics indicating the specific temperatures of the elements to which the sensors are connected or coupled. Instead, the network of sensors represents composite thermal information that is used by the meter electronics to compensate flow and density output information. Since the three sensors are connected in series, the output signal of the network cannot represent the temperature of the balance bar, the case, or any specific flowmeter element.

The purpose of the network of temperature sensors is to output a single temperature signal that can be used in conjunction with the flow tube temperature to accurately predict the change in flow sensitivity of the meter. The location and number of temperature sensors in the network is critical. Meter elements which have a high impact on the thermal stress in the flow tube, such as the balance bar, might have several sensors. Elements such as the flanges have no impact on the thermal stress in the flow tube and they have no temperature sensors. The case temperature has an intermediate impact on tube stress and it has an intermediate number of sensors.

A flowmeter element's impact on flow tube stress is proportional to how much force it can apply to the flow tube. Force from the balance bar is applied directly to the active portion of the flow tube by way of the rigid brace bars. Force from the case is applied to the inactive portions of the flow tube and is divided and resisted by both the active portion of the flow tube and the balance bar. The force exerted by the case thus has less impact than force exerted by the balance bar. In order for the sensor network to output a single temperature representative of thermal stress, it is necessary to weigh the importance of the balance bar more heavily than the case. For instance, if the balance bar temperature has twice the effect as the case temperature, two sensors can be put on the balance bar and one on the case. Wiring these sensors (RTDs) in series gives the total temperature (resistance). Dividing by three gives a weighted average temperature which gives the balance bar temperature twice the importance as the case. In the meter electronics the weighted average network temperature is then subtracted from the tube temperature for the tube stress compensation.

In the above example, it makes no difference whether the case and balance bar are at equal temperatures or different because they are weighted according to their impact on the flow tube stress. For instance, the flow sensitivity is the same whether the tube, balance bar and case are all 70 degrees or whether the tube is 70, the balance bar is 75, and the case is 60. The reason is that the weighted average of (75+75+60)/3 is equal to 70. The physical significance is that the contraction of the 60 degree case is just countered by the expansion of the 75 degree balance bar so that the flow tube experiences no axial load.

Another advantage in using multiple RTDs in series is that for accurate compensation, the average temperature of a component must be used in order to determine the total expansion and force exerted. No one location can give the average temperature. An RTD near the end of the balance bar would register a change in temperature quickly after a change in fluid temperature, but the temperature of the center of the balance bar might lag the end temperature by hours. Having two RTDs on the balance bar in series, one in the center and one near the end, gives a much more accurate representation of the average temperature and thus the expansion of the balance bar. Four RTDs on the balance bar and two on the case would give an even more accurate representation while still keeping the two to one weighting. Or, if the relative importance of the balance bar temperature to case temperature were some other ratio, the appropriate number of RTDs could be placed on each member.

Yet another advantage of the temperature sensor network is that the entire network plus the flow tube sensor only requires three wires (using a common ground wire) through the case feedthrough and to the transmitter. This is important because of the cost of the wires. The present invention does the proper weighting and averaging in the RTD network rather than transmitting all the individual temperatures to the electronics for processing.

The present invention applies the flow tube temperature and the composite temperature of the series sensors along with the time delay between the pickoffs and the resonant frequency of the flow tube to improved material flow and density equations. These equations calculate flow rate and density with improved accuracy over prior art meters.

Aspects of the invention are:

A method and apparatus of providing compensation for output data of a Coriolis flowmeter having a flow tube and a balance bar that are adapted, when in use, to be vibrated in phase opposition;

said flowmeter generates Coriolis deflections of said vibrating flow tube in response to a material flow through said vibrating flow tube;

said method comprising the steps of:

generating a first signal representing the Coriolis deflections of said vibrating flow tube;

generating a second signal representing the temperature of said flow tube;

generating a third signal representing the thermal state of a plurality of elements of said flowmeter exclusive of said flow tube;

using said second signal and said third signal to generate information regarding the thermal state of said flow tube and said plurality of flowmeter elements;

using said information regarding said thermal state to compensate said output data pertaining to said material flowing through said flowmeter.

A method and apparatus wherein the step of generating said second signal comprises the step of obtaining a signal representing the temperature of said flow tube from a sensor coupled to said flow tube; and wherein said step of generating said third signal representing said thermal state of said plurality of elements comprises the steps of:

coupling additional sensors to said plurality of flowmeter elements;

connecting the output of said additional sensors to form a network;

obtaining said third signal from an output of said network representing the composite temperature of said plurality of elements.

A method and apparatus wherein said plurality of elements comprise said balance bar and said case; and wherein said step of coupling said additional sensors comprises the steps of:
  coupling a first sensor to said case;
  coupling at least one sensor to said balance bar;
  connecting outputs of said first sensor and said said at least one additional sensor to form said network.

A method and apparatus wherein said step of connecting the output of said additional sensors comprises the step of:
  connecting the outputs of said additional sensors in series to form said network.

A method and apparatus including the step of extending said network over at least two conductors to meter electronics.

A method and apparatus wherein said step of compensating comprises the step of generating corrected output data pertaining to the mass flow rate of said material.

A method and apparatus wherein said step of generating corrected output data comprises the steps of:
  determining an uncompensated mass flow rate;
  deriving a modulus compensation;
  deriving a thermal stress compensation; and
  using said uncompensated mass flow rate and said modulus compensation and said thermal stress compensation to derive a corrected mass flow rate.

A method and apparatus characterized in that said step of generating said uncompensated flow rate comprises the step of solving the expression $$FCF \cdot (\Delta t_{meas} - \Delta t_0)$$

Where:
FCF=Flow Calibration Factor
$\Delta t_{meas}$=Time delay of pick off signals
$\Delta t_0$=Time delay at zero material flow A method and apparatus characterized in that said step of deriving said modulus compensation comprises the step of solving the expression $$(k_{ft1} \cdot T_f)$$

Where:
$k_{ft1}$=Meter constant based on change in flow tube modulus with temperature
$T_f$=Flow tube temperature A method and apparatus characterized in that said step of deriving said thermal stress compensation comprises the step of solving the expression $$(k_{ft2}(T_f - T_{com}))$$

Where:
$k_{ft2}$=Meter constant based on change in thermal stress with temperature
$T_{ft2}$=Flow tube temperature
$T_{com}$=Temperature of network sensors A method and apparatus characterized in that said step of deriving density compensation comprises the step of solving the expression $$k_{ft3} \cdot (\tau_{ct} - k_2)$$

Where:
$\tau_{ft3}$=Meter constant for density effect on flow
$\tau_{ct}$=Temperature compensated tube vibration period
$k_2$=Tube vibration period constant determined at time of density calibration of flowmeter A method and apparatus characterized in that said step of generating corrected output data comprises the step of deriving a corrected mass flow rate by solving the expression:

$$\dot{m} = FCF \cdot (\Delta t_{meas} - \Delta t_0) \cdot [1 + (k_{ft1} \cdot T_f)] \cdot [1 + k_{ft2}(T_f - T_{com})] \cdot [1 + k_{ft3} \cdot (\tau_{ct} - k_2)]$$

Where;
$\dot{m}$=Mass flow rate
FCF=Flow calibration factor
$\Delta t_{meas}$=Time delay of pick off signals
$\Delta t_0$=Time delay at zero material flow
$k_{ft1}$=Meter constant based on change in flow tube modulus with temperature
$k_{ft2}$=Meter constant based on change in thermal stress with temperature
$k_{ft3}$=Constant for Density effect on flow
$k_2$=Tube vibration period constant determined at time of density calibration of flowmeter
$T_f$=Flow tube temperature
$T_{com}$=Temperature of network sensors
$\tau_{ct}$=Temperature compensated tube vibration period A method and apparatus characterized in that said step of generating corrected output data comprises the step of deriving a corrected mass flow rate by solving the expression:

$$\dot{m} = \dot{m}_{unc}[1 + MOD_{comp}] \cdot [1 + STRESS_{comp}] \cdot [1 + DENSITY_{comp}]$$

Where:
$\dot{m}$=Mass flow rate
$\dot{m}_{unc}$=FCF($\Delta t_{meas} - \Delta t_0$)
$MOD_{comp} = k_{ft1} \cdot T_f$
$STRESS_{comp} = k_{ft2} \cdot (T_f - T_{com})$
$DENSITY_{comp} = k_{ft3} \cdot (\tau_{CT} - k_2)$ A method and apparatus wherein said step of compensating includes the step of deriving corrected output data regarding the density of said material.

A method and apparatus wherein said step of obtaining corrected output data regarding density includes the steps of:
  configuring said flowmeter to input constants from memory;
  calibrating said flowmeter to derive constants;
  determining an uncompensated flow rate;
  determining a compensated tube period corrected for flow;
  determining a tube period corrected for flow, modulus, and stress;
  determining a linear density equation;
  determining a differential tube period equal to the difference between said
  compensated tube period and a flowmeter constant $k_2$ determined during density calibration of said flowmeter;
  multiplying said linear density equation by the sum of 1+ the product of a meter constant $c_3$ times the square of said differential tube period+the product of a flowmeter constant $c_4$ times said differential tube period.

A method and apparatus wherein said step of deriving corrected output data regarding density of said material includes the step of:
  configuring said flowmeter to input constants $a_1$, $a_2$, $c_3$, $c_4$ and $F_d$ from a memory of said meter electronics.

A method and apparatus wherein said step of deriving corrected output data regarding density of said material includes the step of:
  calibrating said flowmeter to determine constants $c_1$, $c_2$, $t_0$, $k_2$ and $\Delta t_0$.

A method and apparatus wherein said step of deriving corrected output data regarding density of said material includes the step of:

determining $\dot{m}_{unc} = FCF(\Delta t_{meas} - \Delta t_0)$

Where:
FCF=Flow Calibration factor
$\Delta t_{meas}$=Time delay of pick off signals
$\Delta t_0$=Time delay at zero flow A method and apparatus wherein said step of deriving corrected output data regarding density of said material includes the step of:

calculating $\tau_{fd} = \tau_m - \dot{m}^2 \cdot F_d$

Where:
$\tau_{fd}$=Compensated tube vibration period for mass flow effect
$\tau_m$=Raw measured flow tube vibration period
$\dot{m}$=Massflow rate
$F_d$=Density flow effect constant A method and apparatus wherein said step of deriving corrected output data regarding density of said material includes the step of:

calculating the expression $\tau_{cp} = \tau_{fd} \cdot \sqrt{1 + a_1 \cdot T_f + a_2 \cdot (T_f - T_{com})}$ Where:
$\tau_{cp}$=Compensated flow tube vibration period for modulus, stress, and flow
$\tau_{fd}$=Compensated tube vibration period for mass flow effect
$a_1$ & $a_2$=Tube vibration period temperature correction constants for modulus and stress $\tau_{fd} = \tau_m - \dot{m}^2 \cdot F_d$=Flow tube vibration period compensation for mass flow $\tau_m$=Raw measured flow tube vibration period
$\dot{m}$=Mass flow rate
$F_d$=Density flow effect constant A method and apparatus wherein the step of deriving corrected output data regarding the density of said material includes the step of calculating the deviation of the material density from that determined by the linear density equation $\rho_m = (c_1 \cdot \tau_{cp}^2 - c_2)$ where $c_1$ and $c_2$ are constants and $\tau_{cp}^2$ is the compensated tube period squared A method and apparatus wherein said step of deriving corrected output data regarding density of said material includes the step of:

modifying the expression $\rho_m = (c_1 \cdot \tau_{cp}^2 - c_2)$ to combine with the non linear components $(1 + c_3 \cdot (\tau_{cp} - k_2)^2 + c_4 \cdot (\tau_{cp} - k_2))$ Where:
$\tau_m$=Raw measured flow tube vibration period
$\tau_{cp}$=Compensated flow tube vibration period for modulus, stress, and flow
$\rho_m$=determined material density
$k_2$=Tube vibration period constant determined at time of material density calibration.
$c_1 c_2 c_3$ & $C_4$=Single tube material density correction constants A method and apparatus wherein said step of deriving corrected output data regarding density of said material includes the step of:

calculating the density of said material from the expression $\rho_m = (c_1 \cdot \tau_{cp}^2 - c_2) \cdot (1 + c_3 \cdot (\tau_{cp} - k_2)^2 + c_4 \cdot (\tau_{cp} - k_2))$ Where:
$\rho_m$=determined material density
$k_2$=Tube vibration period constant determined at time of material density calibration.
$c_3$ & $C_4$=Single tube material density correction constants A method and apparatus wherein the value $\tau_{cp}$ is determined by solving the expression:

$\tau_{cp} = \tau_{fd} \cdot \sqrt{1 + a_1 \cdot T_f + a_2 \cdot (T_f - T_{com})}$ Where:
$a_1 \cdot T_f$=the modulus effect on density
$a_2 (T_f - T_{com})$=the thermal stress effect on density
$a_1$ and $a_2$=are flowmeter constants pertaining to modulus and thermal stress effect on density A method and apparatus wherein said step of deriving corrected output data regarding density includes the step of solving the expression;

$\rho_m = (\text{Density}_{linear})[1 + c_3 (\Delta \text{Period}_{comp})^2 + c_4 (\Delta \text{Period}_{comp})]$ Where:
$\text{Density}_{linear}$=Density determined by linear density equation.
The term $(\Delta \text{Period}_{comp})$ is the difference between the compensated tube vibration period $\tau_{cp}$ (for temperature, stress, and flow) and a tube vibration period constant $k_2$ determined during density calibration of the flowmeter.

A method and apparatus operating a cfm to determine the density of a material flow in said cfm: said method comprising the steps of;
  configuring said cfm to determine meter parameters $a_1$, $a_2$, $c_3$ and $c_4$;
  calibrate said cfm for density of said flowing material using a two point linear calibration method;
  determine calibration coefficients $c_1$ and $c_2$;
  obtain a non-linear calibration curve for said cfm by combining $(1 + c_3 \cdot (\tau_{cp} - k_2)^2 + c_4 \cdot (\tau_{cp} - k_2))$ with said linear calibration curve to negate the deviation of said cfm calibration from linear;
  measure the actual tube period;
  determine a compensated tube period using $a_1$, $a_2$, $T_f$ and $T_{comp}$; and
  determine the density of said material using said non-linear calibration curve.

DESCRIPTION OF THE DRAWINGS

The above and other advantages in features of the invention are best understood when taken in conjunction with the following description thereof together with thee drawings in which.

DETAILED DESCRIPTION

Figure 1:
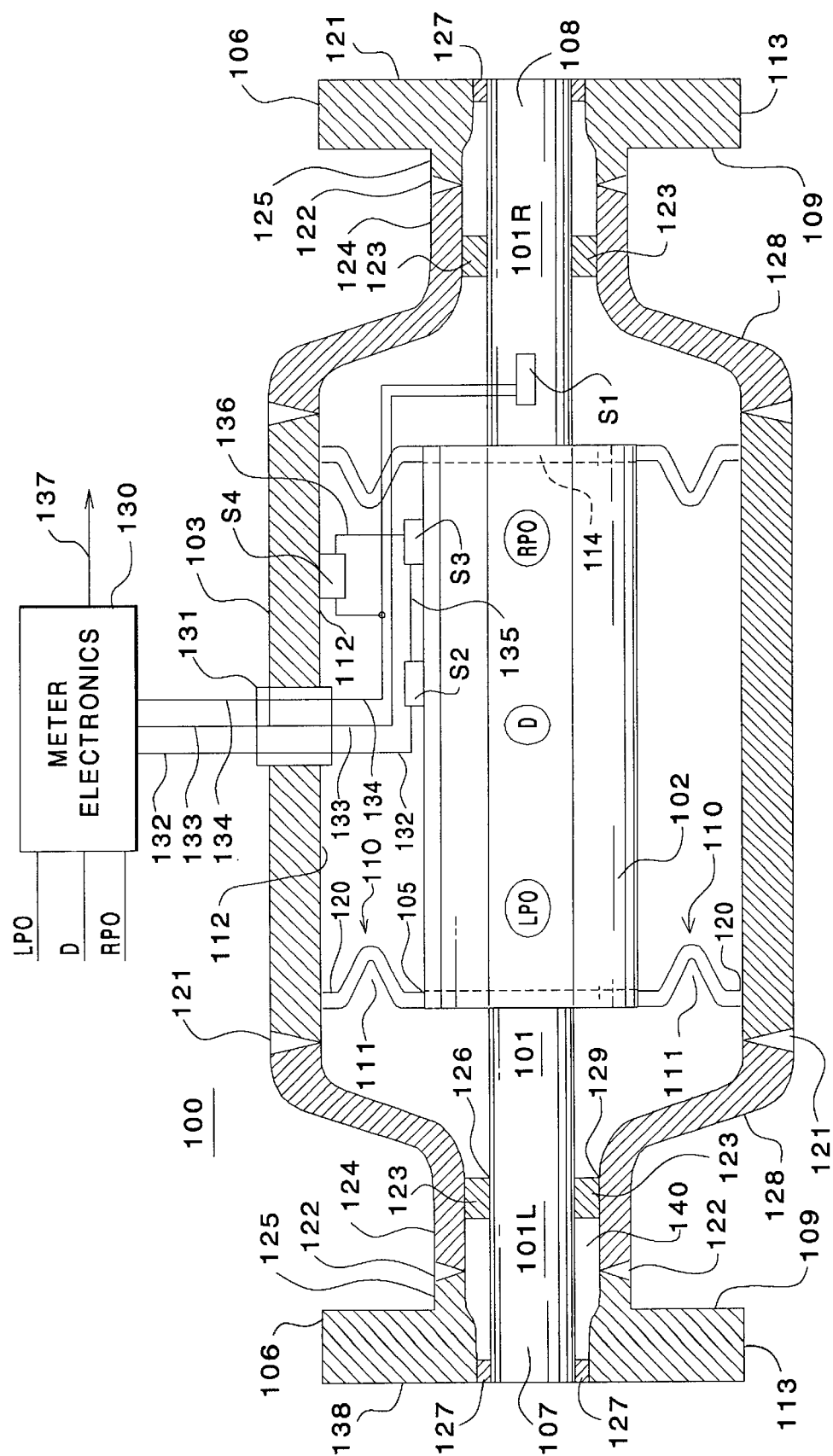
FIG. 1 illustrates a flowmeter embodying the invention.

FIG. 1 discloses a Coriolis flowmeter 100 and meter electronics element 130. Flowmeter 100 has case 103 which encloses flow tube 101 and a surrounding balance bar 102. Flow tube 101 has a left end portion 101L and a right end portion 101R. Flow tube 101 and its ends portions extend the entire length of the flowmeter from the input end 107 to the output end 108 of flow tube 101. Balance bar 102 is connected at its ends 105 to flow tube 101 by circular brace bars 114. Circular brace bars 114 have a center opening for receiving flowtube 101. Ends of balance bar 102 are also connected by a junction at 105 to an inner end of case connect links 110, which are thin strips. The outer ends of case connect links are connected to inner wall 112 of case 103. Each case connect link 110 contains an out of plane bend 111.

Case 103 has an end portion 128 beginning at weld 121 and having a neck 124 extending axially out therefrom to weld element 122 which, in turn, connects to neck 125 of flange 106. Cone connect element 123 is circular and is positioned within the interior of circular neck portion 124 of case end portion 128. Cone connect 123 has a center opening for sealably receiving portions 101L and 101R of flowtube 101. Case connect link 110 and cone connect 123 stabilize balance bar 102 and, in turn, flow tube 101 by preventing undesired translations of these elements with respect to the case wall 103.

Flange 106 has a axially outer surface 138 and an inner opening that includes a lip element 127 which sealably connects flow tube end portions 101L and 101R to flange 106. Surface 113 is the outer circumference of flange 106. Element 109 is the axial inner surface of flange 106. Elements 122 and 121 are welds. Element 125 is a neck of flange 106. Element 105 is a junction at the end of balance bar 102 as well as a junction of an inner radial leg of case connect link 110 and balance bar 102.

In a well known conventional manner, driver D and left pick off LPO and right pick off RPO are coupled to flow tube 101 and balance bar 102. Driver D receives signals over path D (not shown) from meter electronics 130 to cause driver D to vibrate flow tube 101 and balance bar 102 in phase opposition at the resonant frequency of the material filled flow tube 101. The oscillation of vibrating flow tube 101 together with the material flow therein induces Coriolis deflections in the flow tube in a well known manner. These Coriolis deflections are detected by pick offs LPO and RPO with the outputs of these pick offs being transmitted over conductors LPO and RPO (not shown) to meter electronics 130. In a well known manner, the phase difference between the output signals of the pick offs represents information pertaining to material flow within flow tube 101. Meter electronics 130 processes these signals to generate output information that is applied to conductor 137 representing the various parameters of the material flow. These parameters may include density, mass flow rate and other material flow information.

The thermal stress compensation method and apparatus of the present invention is controlled by sensors S1, S2, S3, and S4. Sensor S1 is connected to flow tube 101 and outputs flow tube temperature information over conductors 134 and 133 to meter electronics 130. Sensors S2, S3, and S4 are connected in series to form a network having output conductors 132 and 134. This network transmits information to meter electronics regarding the thermal stresses to which flow tube 101 is subjected. Conductor 134 is the common ground wire to both flow tube sensor S1 and network case sensor S4. Thus, both flow tube sensor S1 and the two wire series network of sensors S2, S3, and S4 share conductor 134. This minimizes the number of conductors that must be extended through feed through 131 to meter electronics 130. Meter electronics may sometimes be located remotely with respect to flowmeter 100. It is desirable to minimize the number of conductors that must be extended through feed through 131 from flowmeter 100 to a remotely situated meter electronics element.

Figure 2:
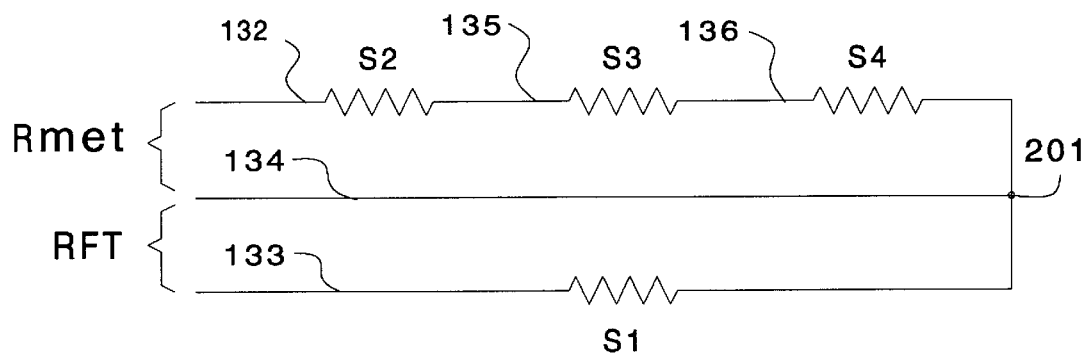
FIG. 2 illustrates the circuitry of a first exemplary embodiment of the invention.

Description of FIG. 2

The circuitry of sensors S1, S2, S3, and S4 is shown on FIG. 2. Flow tube sensor S1 is connected between conductor 133 and common conductor 134. Sensors S2, S3 and S4 are connected in series between conductor 132 and common conductor 134. Terminal 201 is a junction of conductor 134 and sensor S4 and sensor S1. Sensors S1, S2, S3, and S4 may advantageously be RTDs having a nominal resistance of 100 ohms at a nominal temperature of 0° C. The resistance of each RTD varies with changes in temperature by a factor of 0.39 ohm for each 1° C. change in temperature.

RTD S1 is mounted on flow tube 101 and varies its resistance as the flow tube temperature changes. This resistance information is applied over conductors 133 and 134, through feed through 131 to meter electronics 130. Meter electronics 130 processes this information and converts it to flow tube temperature using information programed into a memory of meter electronics 130. Sensors S2 and S3 are mounted on balance bar 102 with sensor S3 being positioned approximate the end of the balance bar and with sensor S2 being positioned near the middle of the balance bar. Sensor S4 is connected to the inner wall 112 of case 103. The stress to which flow tube 101 is subjected is determined primarily by the temperature differential between the flow tube and the balance bar. To a lesser extent, the flow tube stresses are also influenced by the case temperature. Since the balance bar temperature is more important in determining flow tube stresses, the present invention uses two sensors on the balance bar and one sensor on the case wall. Since these three sensors are connected in series and since two of the three sensors are on the balance bar, the network output on conductors 132 and 133 is weighted in favor of the balance bar 102.

The flowmeter may be subject to conditions in which a temperature differential exists between the case and the flow tube on a long term basis. The flowmeter may also be subject to temperature conditions in which the flow tube suddenly changes in temperature when a material of a different temperature passes through the flow tube. Sensors S1 . . . S4 function during the occurrence of all of these conditions to apply information over paths 132, 133, and 134 to meter electronics 130 which processes this information, converts to flow tube stress information and processes it to compensate and correct the output data of the flowmeter.

Figure 3:
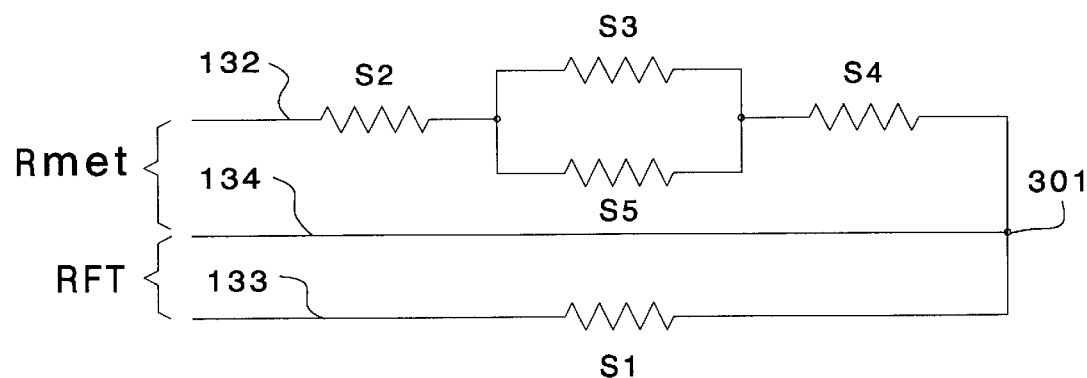
FIG. 3 illustrates the circuitry of a second possible exemplary embodiment of the invention.

Description of FIG. 3

FIG. 3 is a circuit diagram for a temperature network in which two of the sensors are electrically in parallel with each other and in series with the others in the network. If these parallel connected sensors were RTDs, their resistances would be nearly equal and their net resistance would be approximately half of the normal RTD resistance. Sensors in parallel could thus be used in locations that have very little impact on the tube stress, such as the case ends or the case connect links. The "average" temperature of the network of FIG. 3 would be obtained by dividing the total resistance of the network by 2.5.

DESCRIPTION OF MASS FLOW COMPENSATION

Dual curved tube meters, due to their geometry, are immune to the effects of thermal stress and changing fluid specific gravity. Their flow sensitivity is only altered by the effect of temperature on the elastic modulus of the flow tubes. The basic mass flow equation for dual curved tube Coriolis flowmeters is:

$$\dot{m} = FCF \cdot (\Delta t_{meas} - \Delta t_0) \cdot (1 + k_{ft1} T_f) \qquad \text{EQ. 1}$$

Where:
FCF=Flow Calibration Factor (Constant)
$\Delta t_{means}$=Time delay of pickoff signals
$\Delta t_0$=Time delay at zero flow
$k_{ft1}$=Constant based on flow sensitivity change with flow tube modulus
$T_f$=Flow tube temperature For single straight tube flowmeters, the mass flow calibration factor can also shift due to temperature gradients between the case/balance bar and flow tube and due to changing fluid specific gravity. In order to measure the temperature gradient between the elements of a straight tube Coriolis flowmeter, the present invention places three RTD's in series on the flowmeter (two on the balance bar and one on the case) to obtain a composite system temperature. This composite system temperature is then used by the present invention in a mass flow equation for thermal stress compensation. An additional temperature term is added by the present invention to Equation 1 to obtain:

$$\dot{m} = FCF \cdot (\Delta t_{meas} - \Delta t_0) \cdot [1 + (k_{ft1} \cdot T_f)] \cdot [1 + k_{ft2} \cdot (T_f - T_{com})] \qquad \text{EQ. 2}$$

Where:
$k_{ft2}$=constant based on flow sensitivity change with thermal stress
$T_{com} = T_{series}/3$ Where $T_{series}$ is the sum of the 3 RTDs in series The method and apparatus of the present invention further adds one more term to the equation 2 to derive corrected and compensated output data for a straight tube Coriolis flowmeter. The added term compensates for the effect of fluid density on the flow sensitivity of the meter. The explanation of the need for this term follows.

Single tube flowmeters have pickoffs that measure the velocity difference between the flow tube and the balance bar. The pickoff locations on the flow tube experience Coriolis force with flow and time delays between their sinusoidal velocities. The balance bar experiences no direct Coriolis force, thus, there is minimal time delay between the velocities at the balance bar pickoff locations. Since each pickoff output signal is proportional to the difference between the flow tube and balance bar velocities at the pickoff locations, each pickoff signal becomes the vector sum of the phase shifted tube velocity and the minimally phase shifted balance bar velocity. When the fluid density changes, the vibration amplitude ratio between the flow tube and the balance bar changes so as to conserve momentum. This results in the velocity vectors of the flow tube and the balance bar changing length and their vector sums (the output signals of the pickoffs) changing in phase or time delay. It is this change in output signal phase with a change in material density that the density compensation term addresses.

The resulting mass flow equation is:

$$\dot{m} = FCF \cdot (\Delta t_{meas} - \Delta t_0) \cdot [1 + (k_{ft1} \cdot T_f)] \cdot [1 + k_{ft2}(T_f - T_{com})] \cdot [1 + k_{ft3} \cdot (\tau_{ct} - k_2)] \qquad \text{EQ. 3}$$

Where:
$\dot{m}$=Mass flow rate
FCF=Flow Calibration factor
$\Delta t_{meas}$=Time delay of pick off signals
$\Delta t_0$=Time delay at zero flow
$k_{ft1}$=Constant based on change in flow tube modulus with temperature
$k_{ft2}$=Constant based on change in thermal stress with temperature
$k_{ft3}$=Constant for density effect on flow sensitivity
$k_2$=Tube vibration period constant determined at time of density calibration
$T_f$=Flow tube temperature
$T_{com}$=Temperature of network sensors
$\tau_{ct}$=Temperature compensated tube vibration period as discussed in Equation 5.

The terms in EQ. 3 can be better understood by the following grouping:

$$\dot{m} = \dot{m}_{unc}(1 + MOD_{comp})(1 + STRESS_{comp})(1 + DENSITY_{comp}) \qquad \text{EQ. 4}$$

Where:
$\dot{m}_{unc} = FCF(\Delta t_{meas} - \Delta t_0)$
$MOD_{comp} = k_{ft1} \cdot t_1$
$STRESS_{comp} = k_{ft2} \cdot (T_f - T_{com})$
$DENSITY_{comp} = k_{ft3} \cdot (\tau_{ct} - k_2)$ In equation 4 the uncompensated mass flow rate is modified by three compensation terms. The first two terms are compensations for temperature. The first represents the compensation for the change in flow tube modulus $k_{ft1}$ with tube temperature. The second term is the thermal stress term. The thermal stress term is proportional to the difference between the flow tube temperature and the composite temperature produced by the network of temperature sensors. The third compensation term in equation 4 is the compensation for the density effect on flow sensitivity.

Description of Density Compensation of Flow

The compensation for the density effect on flow is, like the thermal stress compensation, improved over prior art by the use of the composite temperature determination provided by the apparatus and method of the present invention. The density compensation term, shown as the $DENSITY_{comp}$ term of mass flow equation 4, consists of two constants, $k_{ft3}$ and $k_2$, and the temperature compensated flow tube vibration period $\tau_{ct}$. The flow tube vibration period is used in the present invention as an indirect measure of material density in the compensation of mass flow rate. The measured flow tube vibration period must be compensated both for the change in the flow tube elastic modulus and the flow tube thermal stress to give a sufficiently accurate indication of the material density compensation effect. Flow rate also has a small effect on the flow tube vibration period. When determining material density, it is therefore necessary to take the flow effect (mass flow rate) into account. At present, however, the flow tube vibration period is only being determined to compensate for the effect of density on the mass flow rate, and the effect of flow rate on tube vibration period is small and can therefore be neglected. The equation for the temperature compensated tube vibration period is:

$$\tau_{ct} = \tau_m \cdot \sqrt{1 + a_1 \cdot T_f + a_2 \cdot (T_f - T_{com})} \qquad \text{EQ. 5}$$

Where:
$\tau_{ct}$=Temperature compensated tube vibration period for mass flow compensation
$\tau_m$=Measured flow tube vibration period
$a_1$ & $a_2$=Density temperature correction constants It will be noted that equation 5 contains under the radical the term $a_1 \cdot T_f$ for change in tube modulus with temperature and the term $a_2 - (T_f - T_{com})$ for the change in stiffness due to thermal stress. The thermal stress term, once again, is determined by the difference between the flow tube temperature and the composite temperature. This equation shows that the determination of the flow tube vibration period compensated for temperature is enhanced over prior art flowmeters by the use of the composite temperature of the flowmeter.

Thus all three compensation terms in the mass flow equation (Equation 3) enhance the accuracy by using the composite temperature of the flowmeter. The thermal modulus and stress terms are directly enhanced while the density effect term (the third compensation term) enhances accuracy by a more accurate determination of the corrected flow tube vibration period. The compensation of mass flow for the density effect, the third compensation term in the mass flow equation 3, requires only the corrected tube vibration period, not the flowing material density.

Discussion of Compensation Interactions

Equations 2, 3, and 4 are structured using the assumption that the compensations for temperature, stress, and flowing material density have interactions. The interactions are compensations on compensations such as a modulus compensation on a density compensation. In equation 4 the number one added to each compensation is the source of the interaction terms. The interactions are only significant when one or more of the compensation terms has a high value compared to the uncompensated flow rate. For instance, if the flowing material density were extremely high (such as mercury), the uncompensated flow rate would be significantly lower than the actual flow rate and the density compensation term would be large. If the modulus and stress compensations were only applied to the uncompensated flow they would be significantly low. By taking into account the interactions, the modulus and stress compensations are also applied to the amount of flow determined by the density compensation.

In general, single straight tube flowmeters have limits on the allowable operating temperature and on the allowable range of fluid density. These limits render the interactions of equation 4 insignificant and equation 5.1 that contains no interactions can be used.

$$\dot{m} = \dot{m}_{unc} + \dot{m}_{unc}[MOD_{comp} + STRESS_{comp} + DENSITY_{comp}] \qquad \text{EQ. 5.1}$$

In general, the more complex equation 4 is not needed because the extreme cases of temperature, stress, and density are generally outside of the allowable limits of the flowmeter.

Description of Density Determination

The equation for the determination of the material density in accordance with the present differs from that of the dual curved tube meter. The density determination equation for a dual curved tube flowmeter is:

$$\rho_m = ((c_1 \cdot \tau_m^2) \cdot (1 + (a_f T_f)) - c_2 \qquad \text{EQ. 6}$$

Where:

$$c_1 = \frac{\rho_w - \rho_a}{\tau_w^2 - \tau_a^2}$$

$\rho_w$=density of water
$\rho_a$=density of air
$\tau_w$=tube vibration period with water
$\tau_a$=tube vibration period with air
$\tau_m$=tube vibration period during operation $$c_2 = \frac{\tau_a^2 \cdot (\rho_w \cdot \rho_a)}{\tau_w^2 - \tau_a^2} - \rho_a$$

$a_1$=constant based on flow tube modulus change with temperature
$T_f$=flow tube temperature Density equation 6 is for dual curved flow tubes. The first term is derived from the equation for the resonant frequency of a vibrating spring mass system. Equation 6 has two additional terms in it. The second term in parentheses is the familiar term for change in flow tube elastic modulus with temperature. The final additional term is the constant $c_2$, which is needed because the flow tube vibration period does not go to zero when the density goes to zero (when the flow tube is empty). The vibration period does not go to zero because the flow tubes have mass even when empty. The constants $c_1$ and $c_2$ are determined by calibrating the meter for density with air and water. Using the known densities for air and water and the measured tube vibration periods, the constants $c_1$ and $c_2$ are calculated for the above equations.

Equation 6 shows that the curved tube flow meter has a term for the shift in the flow tube modulus with temperature but no term for thermal stress. The curved tube geometry renders thermal stress insignificant. Equation 6 also shows that the density is directly proportional to the square of the measured flow tube vibration period with offset $c_2$ due to the fact that the empty flow tube still has mass.

The determination of density of flowing material in a single straight tube flowmeter is more complex than that of a dual curved tube flowmeter as above described in equation 6. Several differences must be considered for single straight tube flowmeters. First, the vibration period of the flow tube must be compensated for thermal stress in addition to modulus change with temperature. Thermal stress compensation is required because the tensioning or compressing of the flow tube can lower or raise the tube vibration period independently of density. Because density is proportional to the tube vibration period squared, the square root of the familiar compensations for stress and modulus change is used to compensate the tube vibration period.

Second, the flowtube vibration period must be compensated for mass flow effect. U.S. Pat. No. 5,295,804 shows that the period of the vibrating flow tube increases slightly with high flow rates. Compensation must be made for the mass flow effect or the density readings at high flow rates will be erroneously high. This compensation can also be used to improve the accuracy of dual and curved tube meters. The improved equation of the present invention for determining the compensated flow tube vibration period is:

$$\tau_{cp} = \tau_{fd} \cdot \sqrt{1 + a_1 \cdot T_f + a_2 \cdot (T_f - T_{com})} \qquad \text{EQ. 7}$$

Where:

$\tau_{cp}$=Compensated flow tube vibration period for modulus, stress, and flow $\tau_{fd}$=Compensated tube vibration period for mass flow effect $a_1$ & $a_2$=Tube vibration period temperature correction constants for modulus and stress $\tau_{fd} = \tau_m - \dot{m}^2 \cdot F_d$=Flow tube vibration period compensation for mass flow $\tau_m$=Raw measured flow tube vibration period $\dot{m}$=Mass flow rate (can be estimated by $\Delta t_{meas} - \Delta t_0$)

$F_d$=Density flow effect constant

The density calibration is normally done before the flow calibration because the density calibration can be done with no flow which causes the flow compensation term, $\tau_{fd}$, in equation 7 to be equal to the raw measured tube vibration period. The constants $a_1$ and $a_2$ as well as $F_d$ are meter constants that are the same for all meters of a given size. They are determined through extensive testing and are entered into the meter electronics when the meter is configured.

The density equation requires the use of the compensated tube vibration period $\tau_{cp}$ of equation 7. The density determination of a single tube flowmeter differs from that of a dual tube flowmeter in that the density is not quite proportional to the square of the compensated tube vibration period for a single tube meter. Density is not proportional to the tube vibration period squared for a single tube meter because changing fluid density causes the movement of the nodes which define the ends of the flow tube and the balance bar. Movement of these nodes causes an effective mass transfer between the flow tube and the balance bar. The mass transfer causes the graph of fluid density versus tube vibration period squared to be a curve rather than the straight line of dual tube meters.

It is therefore necessary that the equation for determining the density of a fluid have additional terms (beyond those of equation 6). The relationship between the compensated tube vibration period and the material density is shown by the following equation:

$$\rho_m = (c_1 \cdot \tau_{cp}^2 - c_2) \cdot (1 + c_3 \cdot (\tau_{cp} - k_2)^2 + c_4 \cdot (\tau_{cp} - k_2)) \quad \text{EQ. 8}$$

Where:

$\rho_m$=flowing material density $c_1$ & $c_2$=constants determined by a two point density calibration $k_2$=Tube vibration period constant determined at time of density calibration.

$C_3$ & $C_4$=Straight tube density correction constants

The first term in parenthesis in equation 8 is the linear density term of equation 6. The constants $c_1$ and $c_2$ are determined through air and water calibrations as for equation 6. The additional terms in equation 8 provide the density compensation for change in modulus, stress, and flow. The additional terms also provide for the effective mass transfer between the flow tube and the balance bar with changes in density. The constants for these terms, $c_3$ and $c_4$, determine the deviation from the linear relationship of dual tube meters. They are constant for a given meter size and are determined through extensive testing. $c_3$ and $c_4$ do not require calibration for each meter.

Figure 4:
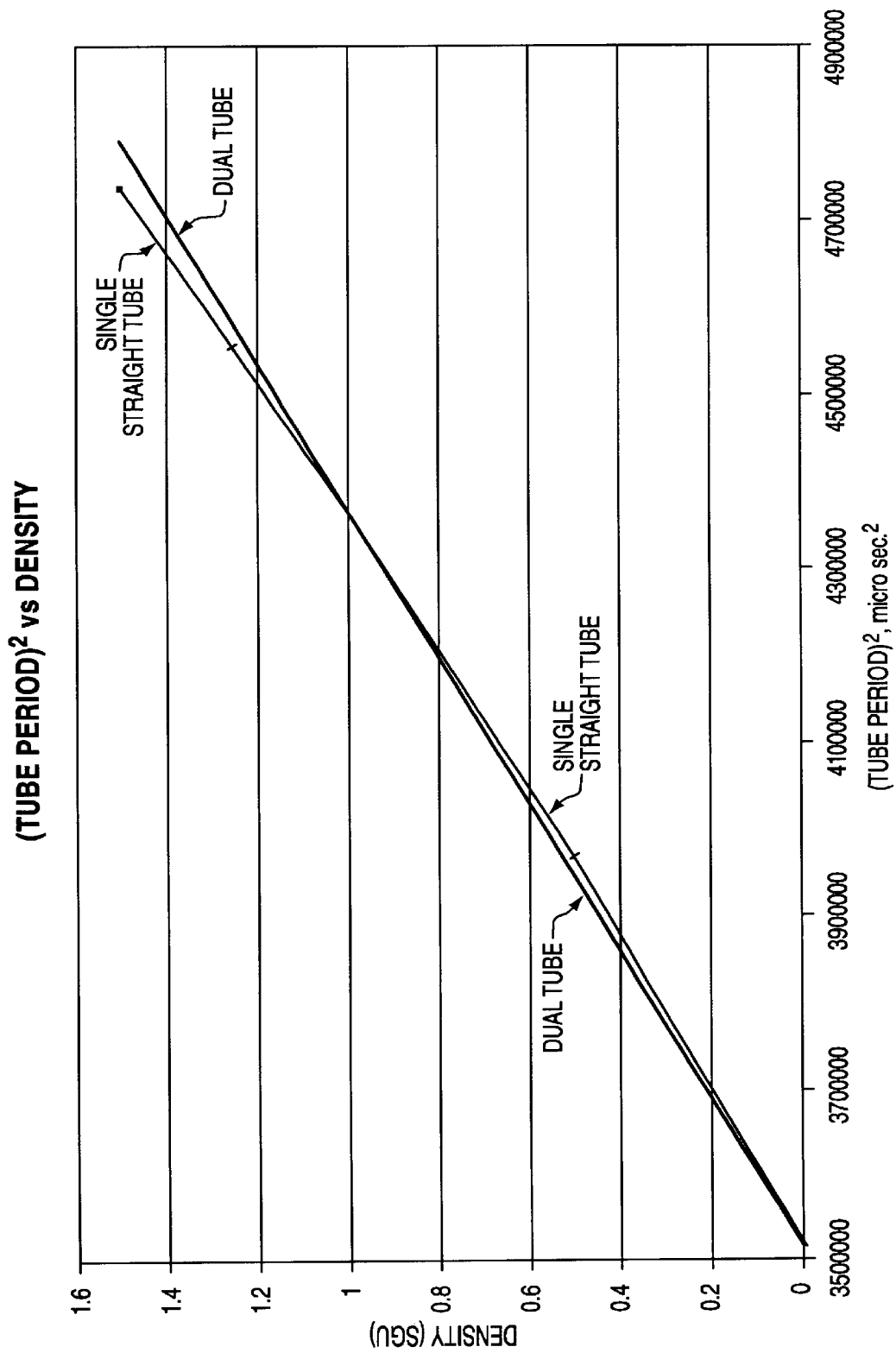
FIG. 4 is a graph of tube vibration period squared versus density.

Description of FIG. 4

FIG. 4 is a graph of the tube vibration period squared versus the material density for a single straight tube meter and a dual curved tube meter. The line representing the dual tube meter is straight. This linear relationship enables dual tube meters to be calibrated for density on two materials, air and water, since two points define a straight line. The curve representing the single straight tube meter deviates from the straight line. It deviates because of the change in position of the nodal regions as discussed earlier. For a single straight tube meter, the use of the straight line obtained by an air and water calibration, as is done for dual tube meters, would under estimate the density for materials heavier than water and would over estimate the density for materials lighter than water. The non linear calibration curve representing the single straight tube meter in FIG. 4 could be determined by performing a calibration using more than two materials of different densities. However, it would be time consuming and expensive to use calibration points on a materials other than air and water for meter calibration.

Figure 5:
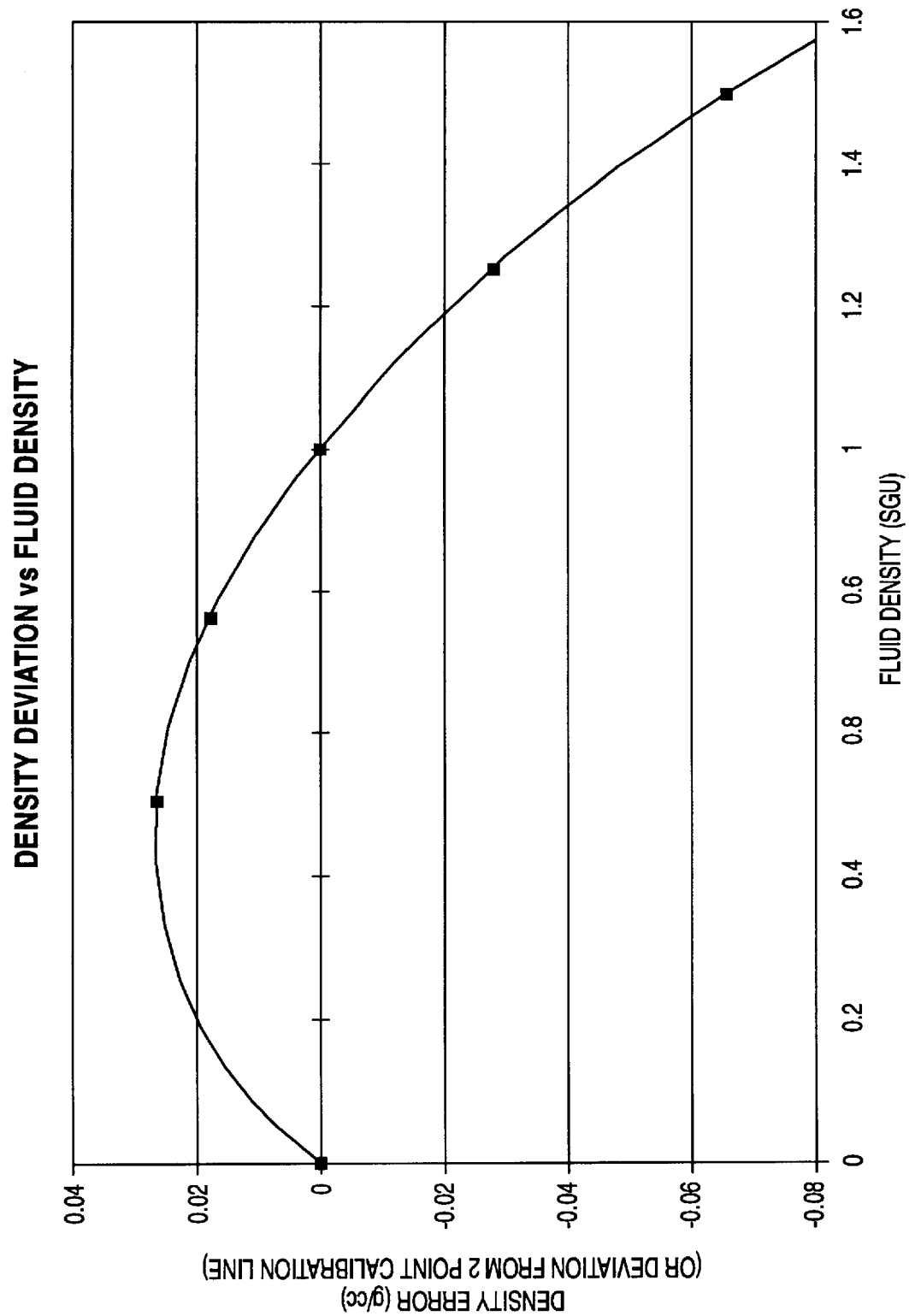
FIG. 5 is a graph of density error v.s. density.

Description of FIG. 5

FIG. 5 shows a graph of the density error that would result from using the standard (dual tube) linear density equation of FIG. 4 on a single tube meter. It can be seen that the density error is zero at both the air density point of zero and the water density point of one. The density error is positive for lower density materials and negative for higher density materials. This graph can also be considered the deviation of the density output curve of the single straight tube meter from the use of the straight line produced by two point calibrations.

Figure 6:
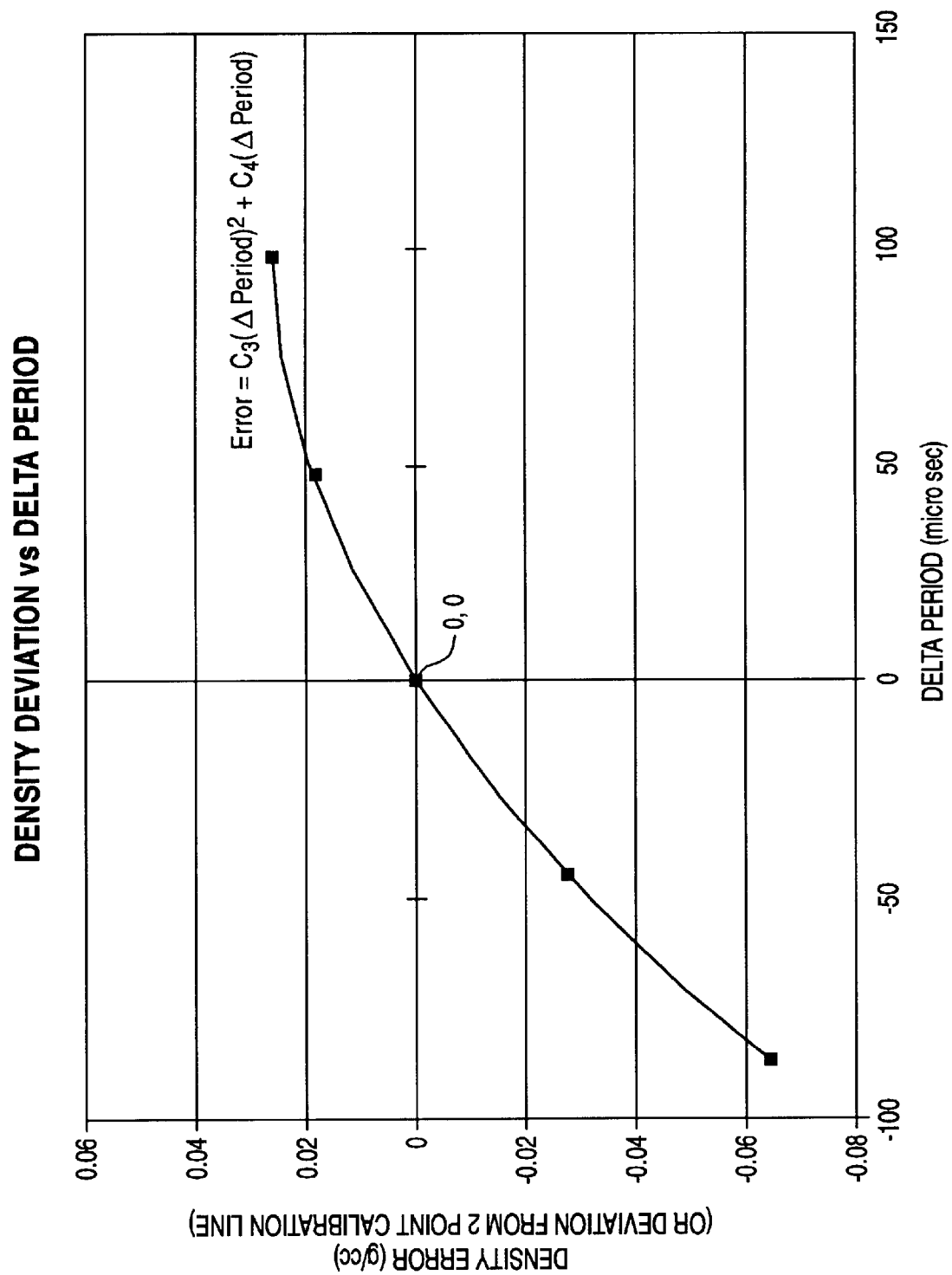
FIG. 6 is a graph showing density error v.s. change in tube vibration period.

Description of FIG. 6

FIG. 6 is another way of showing the density error (deviation) data of FIG. 5. This graph of FIG. 6 shows density error (or deviation from the linear calibration line) versus the difference between the measured tube vibration period and the water filled tube vibration period (both corrected for flow and temperature). The density deviation is the difference between the actual material density and the predicted density using the straight line generated by the air-water density calibrations of FIG. 4. This method of presenting the deviation data puts the graph origin (0,0) at the water density calibration point. It also allows for a relatively simple equation of the curve of the data points. The equation for the density deviation from using a linear two point calibration with a single straight tube meter is shown on FIG. 6.

The present invention includes a new calibration method for determining the density in single straight tube meters that has the accuracy of three point calibrations while only using air and water density calibrations. Using the new method, a two point calibration is done yielding the usual straight line. This line varies from meter to meter for even the same size meter. This line varies in both slope and the tube vibration period with water. However, the method of the present invention makes use of the fact that all the meters of a given size have the same deviation from the two point calibration line (similar to that shown in FIG. 6). This curve contains the deviation of the actual density points from the straight line. The 0,0 point on the deviation curve is located at the water calibration point on the straight line of the two point calibration.

In the present invention, the air-water slope and the tube vibration period for water are determined by an air water calibration ($c_1$ and $c_2$). The equation of the deviation from this straight line is stored in the meter electronics memory for each meter size. The equation constants for the deviation from this line are $c_3$ and $c_4$ in the density equation 8. They are determined through extensive testing. The values of $c_3$ and $c_4$ are different for each meter size. The meter electronics knows what size meter is in use because it is entered during the initial setup of the meter. The meter electronics determines the true material density by subtracting a deviation from the straight line of the two point calibration. The subtracted deviation is determined by the deviation equation stored in the memory of the meter electronics.

Therefore, in the present invention, the meter electronics determines density by correcting for modulus change with temperature, by correcting for thermal stress using an improved method of determining the composite meter temperature, by correcting for mass flow rate, and by using an improved compensation method that compensates for non-linearity in the density versus tube vibration period squared curve.

Figure 7:
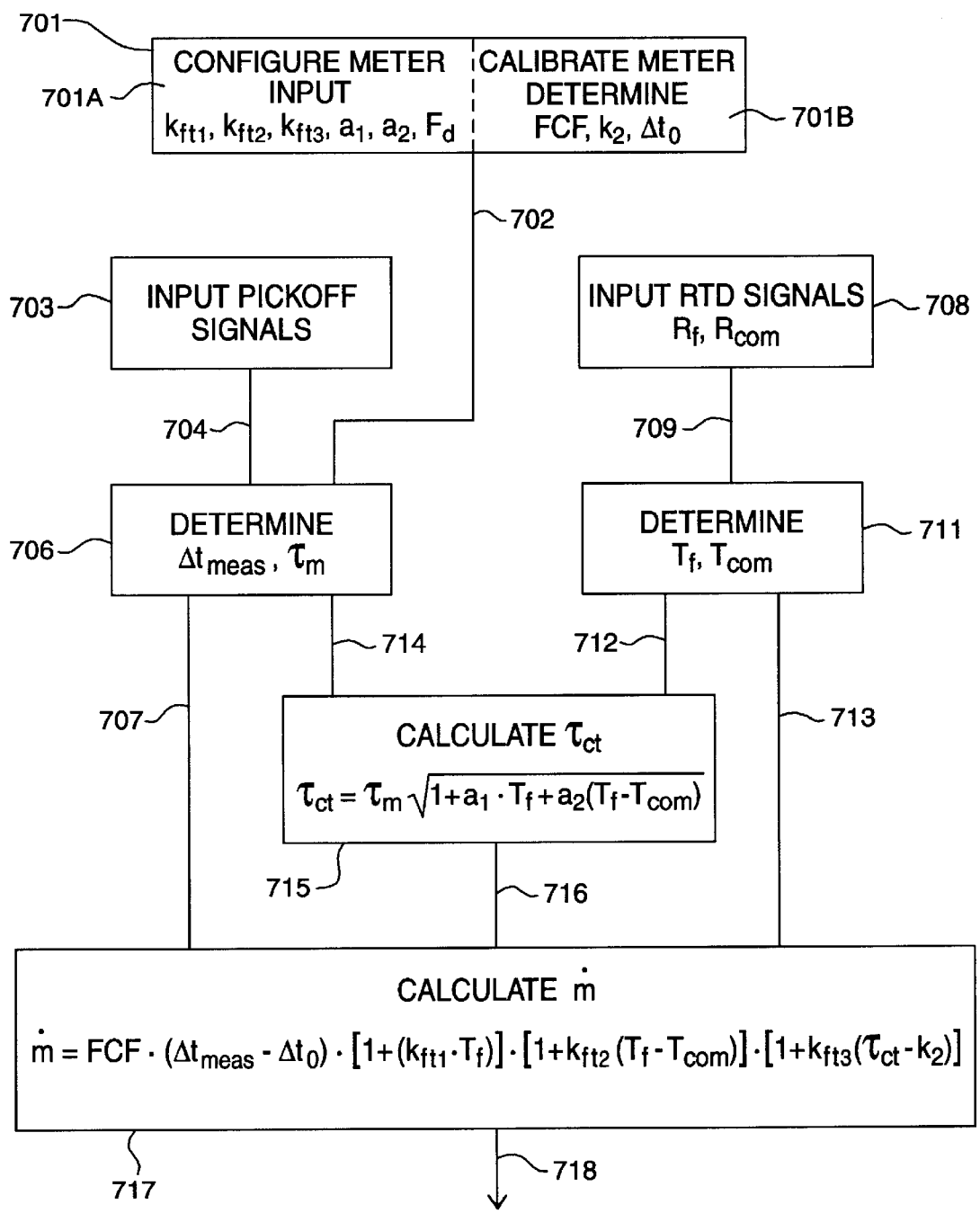
FIG. 7 illustrates a flow chart for the method of the invention that determines material mass flow rate.

Description of FIG. 7

FIG. 7 is a block diagram that describes the manner in which the present invention performs its compensation function of the mass flow rate. The block diagram of FIG. 7, as well as of FIG. 8, discloses a plurality of processing or program steps each representing one or more program instructions stored in a memory of meter electronics 130. The instructions are executed by a C.P.U. of meter electronics with the results either being stored in memory or outputted to a user over path 137.

The flowmeter is configured and calibrated in step 701 which contains two steps 701A and 701B. Step 701A inputs the constants $k_{ft1}$, $k_{ft2}$, $k_{ft3}$, $a_1$, $a_2$, and $F_d$ from memory of meter electronics 130. Step 701B calibrates the flowmeter and determines the elements FCF, $k_2$, and $\Delta t_0$. The output information of steps 701A and 701B is applied over path 702 to step 706. Step 703 represents the sinusoidal pickoff signals of the meter. They are transmitted over path 704 to step 706. Step 706, extracts the time delay produced by the flow, $\Delta t_{meas}$, and the vibration period of the flow tube, $\tau_m$. Step 708 represents the resistances of the flow tube RTD and the network of RTDs. The resistances are transmitted via path 709 to step 711 of meter electronics where they are converted to the tube temperature and the composite temperature.

The raw vibration period of the flow tube from step 706 and the temperatures from step 711 are transmitted by paths 714 and 712 to step 715 which calculates the flow tube vibration period $\tau_m$ corrected for temperature. The corrected tube vibration period $\tau_{ct}$ is then transmitted via path 716 to step 717. Step 717 also receives the time delay at zero flow $\Delta t_0$ and the time delay $\Delta t_{meas}$ produced by the flow via path 707 from step 706 as well as the flow tube and composite temperatures via path 713 from step 711.

In step 717 the compensated mass flow equation is applied as inputs from steps 706, 715, and 711. The compensated mass flow rate $\dot{m}$ is then output via path 718 to the users application (not shown). Also not shown in FIG. 7 are the paths from memory of meter electronics (step 701) where the constants are stored to the steps where they are used.

Figure 8:
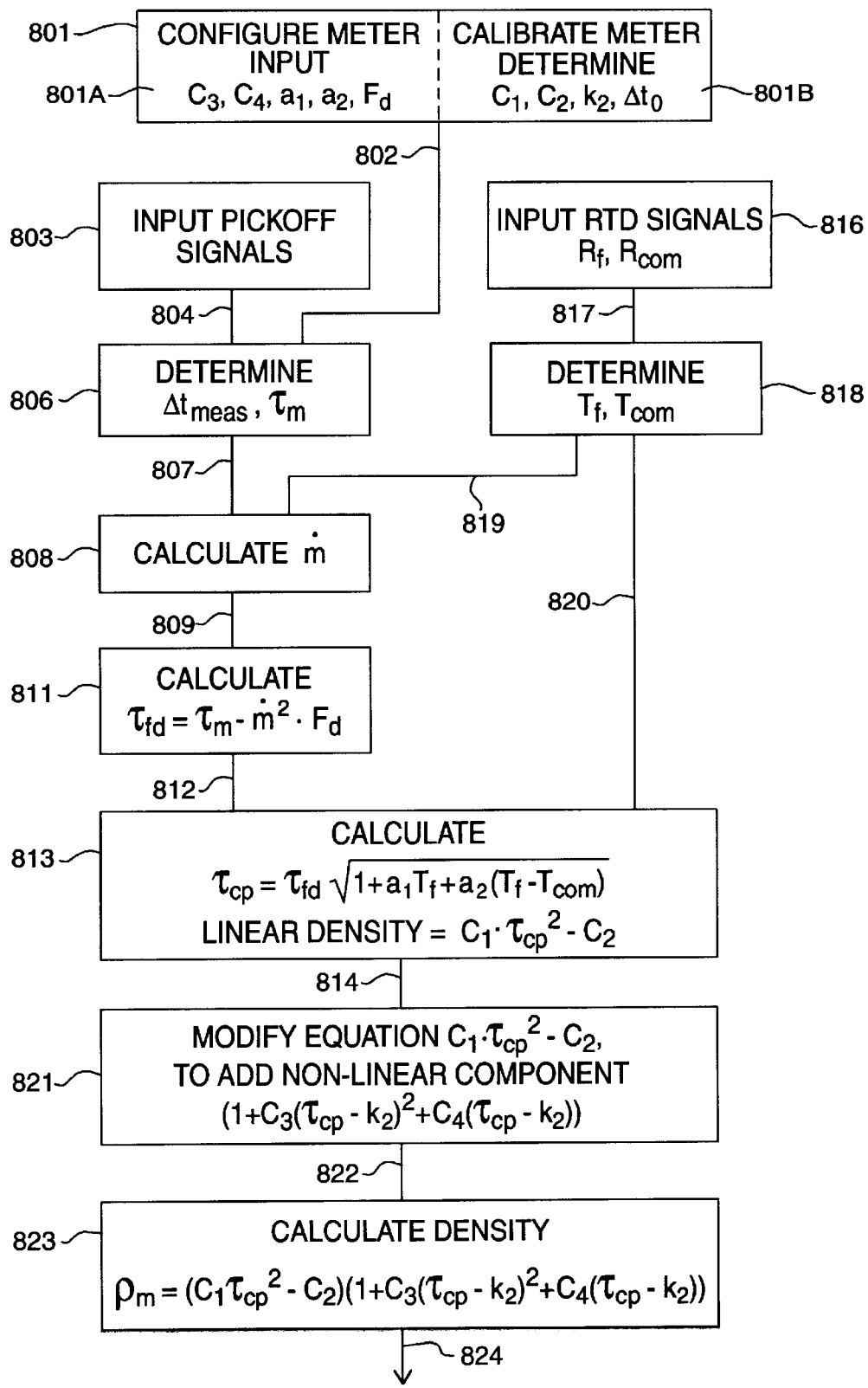
FIG. 8 illustrates a flow chart for the method of the invention that determines material density.

Description of FIG. 8

FIG. 8 is a block diagram that describes the manner in which the program instructions of the present invention perform a its compensation function of the material density output. The meter is configured and calibrated in step 801 which consists of steps 801A and 801B. In step 801A, constants $c_3$, $c_4$, $a_1$, $a_2$, and $F_d$ are input from the memory of meter electronics 130. Step 801B generates symbols $c_1$, $c_2$, $\Delta t_0$, and $k_2$ through meter calibration. The output of step 801 is applied over path 802 to step 806. Step 803 represents the sinusoidal pickoff signals. These pickoff signals are input to meter electronics of step 806 via path 804. In step 806 the time delay $\Delta t_{means}$ due to flow and the raw vibration period $\tau_m$ of the flow tube are determined. Meanwhile, the RTD signals of step 816 are transmitted via path 817 to step 818 where they are converted to temperature. Step 808 receives time delay at zero flow $\Delta t_0$ from step 801 (path not shown), time delay $\Delta t_{meas}$ due to flow, and the raw flow tube vibration period $\tau_m$ from step 806 via path 807. Step 808 also receives the material temperature and the composite temperature $T_{com}$ from step 818 via path 819. In step 808 the mass flow rate $\dot{m}$ is calculated as described in FIG. 7. The mass flow rate $\dot{m}$ is applied via path 809 to step 811 where it is used along with the raw tube vibration period to calculate the tube vibration period $\tau_{fd}$ compensated for mass flow rate. This is then applied via path 812 to step 813 where it is used along with the temperatures from step 818 via path 820 to calculate the tube vibration period $\tau_{cp}$ further compensated for modulus shift with temperature as well as with thermal stress. All the parameters are now known to solve the linear density equation show in step 813.

The fully compensated tube vibration period $\tau_{cp}$ is then transmitted via path 814 to step 821 which modifies the linear compensation equation $c_1 \cdot \tau_{cp}^2 - c_2$ from step 806 by combining it with the non linear compensation term $(1+c_3 \cdot (\tau_{cp}-k_2)^2 + c_4 \cdot (\tau_{cp}-k_2))$. This non linear term is combined with the linear equation of step 806 to form the complete density equation which is passed over path 822 to step 823. Step 823 receives this information and calculates the material density $\rho_m$. The material density $\tau_m$ is the transmitted via path 822 to an output application (not shown). Also not shown in FIG. 8 are the paths from memory (step 801) where the constants are stored to the steps where they are used.

It is to be expressly understood that the claimed invention is not to be limited to the description of the preferred embodiment but encompasses other modifications and alterations within the scope and spirit of the inventive concept. For example, although the present invention has been disclosed as comprising a part of a single straight tube Coriolis flowmeter, it is to be understood that the present invention is not so limited and may be used with other types of Coriolis flowmeters including single tube flowmeters of irregular or curved configuration as well as Coriolis flowmeters having a plurality of flow tubes.

Thus, the use of the term "material" is to be understood as including fluids, gasses, plasma as well as any and all substances that can flow through a flow meter for a determination and measurement of information pertaining to said materials. Also, while specific relationships and equations have been described in connection with the invention, it is to be understood that the invention includes and may be practiced using modifications of the disclosed equations and relationships.

What is claimed is:

1. A method of providing compensation for output data of a Coriolis flowmeter having a flow tube and a balance bar that are adapted, when in use, to be vibrated in phase opposition;

said flowmeter generates Coriolis deflections of said vibrating flow tube in response to a material flow through said vibrating flow tube;

said method comprising the steps of:

generating a first signal representing the Coriolis deflections of said vibrating flow tube;

generating a second signal representing the temperature of said flow tube;

generating a third signal representing the thermal state of a plurality of elements of said flowmeter exclusive of said flow tube;

using said second signal and said third signal to generate information regarding the thermal state of said flow tube and said plurality of flowmeter elements;

using said information regarding said thermal state to compensate said output data pertaining to said material flowing through said flowmeter.

2. The method of claim 1 wherein the step of generating said second signal comprises the step of obtaining a signal representing the temperature of said flow tube from a sensor coupled to said flow tube; and wherein said step of generating said third signal representing said thermal state of said plurality of elements comprises the steps of:

coupling additional sensors to said plurality of flowmeter elements;

connecting the output of said additional sensors to form a network;

obtaining said third signal from an output of said network representing the composite temperature of said plurality of elements in response to the receipt by said network of said signals applied by said additional sensors.

3. The method of claim 2 wherein said plurality of elements comprise said balance bar and said case; and wherein said step of coupling said additional sensors comprises the steps of:

coupling a first sensor to said case;

coupling at least one sensor to said balance bar;

connecting outputs of said first sensor and said at least one additional sensor to form said network.

4. The method of claim 3 wherein said step of connecting the output of said additional sensors comprises the step of:

connecting the outputs of said additional sensors in series to form said network.

5. The method of claim 4 including the step of extending said network over at least two conductors to meter electronics.

6. The method of claim 1 wherein said step of compensating comprises the step of generating corrected output data pertaining to the mass flow rate of said material.

7. The method of claim 6 wherein said step of generating corrected output data comprises the steps of:

determining an uncompensated mass flow rate;

deriving a modulus compensation;

deriving a thermal stress compensation; and using said uncompensated mass flow rate and said modulus compensation and said thermal stress compensation to derive a corrected mass flow rate.

8. The method of claim 7 characterized in that said corrected mass flow rate is obtained by the step of multiplying said uncompensated mass flow rate by 1 plus 1+ said thermal stress compensation.

9. The method of claim 7 wherein said step of generating corrected output data comprises the further steps of:

deriving a density compensation;

multiplying said uncompensated mass flow rate by 1 plus said stress compensation and 1+ said modulus compensation and 1+ said density compensation to obtain a corrected mass flow rate.

10. The method of claim 7 characterized in that said step of generating said uncompensated flow rate comprises the step of solving the expression $$FCF \cdot (\Delta t_{meas} - \Delta t_0)$$

Where:
FCF=Flow Calibration Factor
$\Delta t_{meas}$=Time delay of pick off signals
$\Delta t_0$=Time delay at zero material flow.

11. The method of claim 7 characterized in that said step of deriving said modulus compensation comprises the step of solving the expression $$(k_{ft1} \cdot T_f)$$

Where:
$k_{ft1}$=Meter constant based on change in flow tube modulus with temperature
$T_f$=Flow tube temperature.

12. The method of claim 7 characterized in that said step of deriving said thermal stress compensation comprises the step of solving the expression $$(k_{ft2}(T_f - T_{com}))$$

Where:
$k_{ft2}$=Meter constant based on change in thermal stress with temperature
$T_f$=Flow tube temperature
$T_{com}$=Temperature of network sensors.

13. The method of claim 9 characterized in that said step of deriving said density compensation comprises the step of solving the expression $$k_{ft3} \cdot (\tau_{ct} k_2)$$

Where:
$k_{ft3}$=Meter constant for density effect on flow
$\tau_{ct}$=Temperature compensated tube vibration period
$k_2$=Tube vibration period constant determined at time of density calibration of flowmeter.

14. The method of claim 6 characterized in that said step of generating corrected output data comprises the step of deriving a corrected mass flow rate by solving the expression:

$$\dot{m}=FCF \cdot (\Delta t_{meas}-\Delta t_0) \cdot [1+(k_{ft1} \cdot T_f)] \cdot [1+k_{ft2}(T_f-T_{com})] \cdot [1+k_{ft3} \cdot (\tau_{ct}-k_2)]$$

Where:
$\dot{m}$=Mass flow rate
FCF=Flow Calibration factor
$\Delta t_{meas}$=Time delay of pick off signals
$\Delta t_0$=Time delay at zero flow
$k_{ft1}$=Meter constant based on change in flow tube modulus with temperature
$k_{ft2}$=Meter constant based on change in thermal stress with temperature
$k_{ft3}$=Meter constant for density effect on flow
$k_2$=Tube vibration period constant determined at time of density calibration of flowmeter
$T_f$=Flow tube temperature
$T_{com}$=Temperature of network sensors
$\tau_{ct}$=Temperature compensated tube vibration period.

15. The method of claim 6 characterized in that said step of generating corrected output data comprises the step of deriving a corrected mass flow rate by solving the expression:

$$\dot{m}=\dot{m}_{unc}\cdot[1+MOD_{comp}]\cdot[1+STRESS_{comp}]\cdot[1+DENSITY_{comp}]$$

Where:
$\dot{m}$=Mass flow rate
FCF=Flow calibration factor
$\Delta t_{meas}$=Time delay of pick off signals
$\Delta t_0$=Time delay at zero material flow
$k_{ft1}$=Meter constant based on change in flow tube modulus with temperature
$k_{ft2}$=Meter constant based on change in thermal stress with temperature
$\dot{m}^{unc}=FCF(\Delta t_{meas}-\Delta t_0)$
$MOD_{comp}=k_{ft1}\cdot T_f$
$k_{ft3}$=Constant for Density effect on flow
$k_2$=Tube vibration period constant determined at time of density calibration of flowmeter
$T_f$=Flow tube temperature
$T_{com}$=Temperature of network sensors
$\tau_{ct}$=Temperature compensated tube vibration period
$STRESS_{comp}=k_{ft2}\cdot(T_f-T_{com})$
$DENSITY_{comp}=k_{ft3}\cdot(\tau_{CT}-k_2)$.

16. The method of claim 1 wherein said step of compensating includes the step of deriving corrected output data regarding the density of said material.

17. The method of claim 16 wherein said step of obtaining corrected output data regarding density includes the steps of:
configuring said flowmeter to input constants from memory;
calibrating said flowmeter to derive constants;
determining an uncompensated flow rate;
determining a compensated tube period corrected for flow;
determining a tube period corrected for flow, modulus, and stress;
determining a linear density equation;
determining a differential tube period equal to the difference between said compensated tube period and a flowmeter constant $k_2$ determined during density calibration of said flowmeter;
multiplying said linear density equation by the sum of 1+ the product of a flowmeter constant $c_3$ times the square of said differential tube period+the product of a flowmeter constant $c_4$ times said differential tube period.

18. The method of claim 17 wherein said step of deriving corrected output data regarding density of said material includes the step of:
configuring said flowmeter to input constants $a_1,a_2,c_3,c_4$, and $F_d$ from a memory of said meter electronics,
Where:
$F_d$=Density flow effect constant
$a_1$ & $a_2$=Tube vibration period temperature correction constants for modulus and stress
$c_3$&$c_4$=Single tube material density correction constants.

19. The method of claim 17 wherein said step of deriving corrected output data regarding density of said material includes the step of:
calibrating said flowmeter to determine constants $c_1$, $c_2$, $k_2$, and $\Delta t_0$
Where:
$\Delta t_0$=Time delay at zero flow
$k_2$=Tube vibration period constant determined at time of density calibration of flowmeter
$c_1$ and $c_2$ are constants.

20. The method of claim 17 wherein said step of deriving corrected output data regarding density of said material includes the step of:

$$\text{determining } \dot{m}_{unc}=FCF(\Delta t_{meas}-\Delta t_0)$$

Where:
$\dot{m}_{unc}$=the uncompensated mass flow rate
FCF=Flow Calibration factor
$\Delta t_{meas}$=Time delay of pick-off signals
$\Delta t_0$=Time delay at zero flow.

21. The method of claim 17 wherein said step of deriving corrected output data regarding density of said material includes the step of:

$$\text{calculating } \tau_{fd1}=\tau_m-\dot{m}^2\cdot F_d$$

Where:
$\tau_{fd}$=Compensated tube vibration period for mass flow effect
$\tau_m$=Raw measured flow tube vibration period
$\dot{m}$=Mass flow rate
$F_d$=Density flow effect constant.

22. The method of claim 17 wherein said step of deriving corrected output data regarding density of said material includes the step of:
calculating the expression $$\tau_{cp}=\tau_{fd}\cdot\sqrt{1+a_1\cdot T_f+a_2\cdot(T_f-T_{com})}$$

Where:
$T_f$=Flow tube temperature
$T_{com}$=Temperature of network sensors
$\tau_{cp}$=Compensated flow tube vibration period for modulus, stress, and flow
$\tau_{fd}$=Compensated tube vibration period for mass flow effect
$a_1$ & $a_2$=Tube vibration period temperature correction constants for modulus and stress
$\tau_{fd}=\tau_m-\dot{m}^2\cdot F_d$=Flow tube vibration period compensation for mass flow
$\tau_m$=Raw measured flow tube vibration period
$\dot{m}$=Mass flow rate
$F_d$=Density flow effect constant.

23. The method of claim 17 wherein the step of deriving corrected output data regarding the density of said material includes the step of calculating the deviation of the material density from that determined by the linear density equation $$\rho_m=(c_1\cdot\tau_{cp}^2-c_2)$$

where $c_1$ and $c_2$ are constants and $\tau_{cp}^2$ is the compensated tube period squared.

24. The method of claim 17 wherein said step of deriving corrected output data regarding density of said material includes the step of:
modifying the expression $$\rho_m=(c_1\cdot\tau_{cp}^2-c_2)$$

to add the non linear components $$(1+c_3\cdot(\tau_{cp}-k_2)^2+c_4\cdot(\tau_{cp}-k_2))$$

Where:
$\tau_m$=Raw measured flow tube vibration period
$\tau_{cp}$=Compensated flow tube vibration period for modulus, stress, and flow $\rho_m$=determined material density $k_2$=Tube vibration period constant determined at time of material density calibration $c_1, c_2, c_3, \& c_4$=Single tube material density correction constants.

25. The method of claim 17 wherein said step of deriving corrected output data regarding density of said material includes the step of:

calculating the density of said material from the expression $$\rho_m = (c_1 \cdot \tau_{cp}^2 - c_2) \cdot (1 + c_3 \cdot (\tau_{cp} - k_2)^2 + c_4 \cdot (\tau_{cp} - k_2))$$

Where:

$\rho_m$=determined material density $k_2$=Tube vibration period constant determined at time of material density calibration $c_1, c_2, c_3, \& c_4$=Single tube material density correction constants $\tau_{cp}$=Compensated flow tube vibration period for modulus, stress, and flow.

26. The method of claim 25 wherein the value $\tau_{cp}$, is determined by solving the expression:

$$\tau_{cp} = \tau_{fd} \cdot \sqrt{1 + a_1 \cdot T_f + a_2 \cdot (T_f - T_{com})}$$

Where:

$T_f$=Flow tube temperature $T_{com}$=Temperature of network sensors $a_1 \cdot T_f$=the modulus effect on density $a_2(T_f - T_{com})$=the thermal stress effect on density $a_1$ and $a_2$ are flowmeter constants pertaining to modulus and thermal stress effect on density.

27. The method of claim 17 wherein said step of deriving corrected output data regarding density includes the step of solving the expression;

$$\rho_m = (\text{Density}_{linear})[1 + c_3(\Delta\text{Period}_{comp})^2 + c_4(\Delta\text{Period}_{comp})]$$

Where:

$\text{Density}_{linear} = \rho_m = c_1 \cdot \tau_{cp}^2 - c_2$ $c_1$ and $c_2$ are constants and $\rho_m$=determined material density $c_3 \& c_4$=Single tube material density correction constants and the term ($\Delta\text{Period}_{comp}$) is the difference between the compensated tube vibration period $\tau_{cp}$ (for temperature, stress, and flow) and a tube vibration period constant $k_2$ determined during density calibration of the flowmeter.

28. Apparatus that provides thermal stress compensation for output data of a Coriolis flowmeter having a flow tube and a balance bar that are adapted, when in use, to be vibrated in phase opposition in a drive plane; said flowmeter generates Coriolis deflections of said vibrating flow tube in response to a material flow through said vibrating flow tube; said apparatus comprises:

apparatus that generates a first signal representing the Coriolis deflections of said vibrating flow tube;

apparatus that generates a second signal representing the temperature of said flow tube;

apparatus that generates a third signal representing the thermal state of a plurality of elements of said flowmeter exclusive of said flow tube;

meter electronics that receives said second and third signals and generates information regarding the thermal state of said plurality of flowmeter elements; and said meter electronics uses said thermal state information to compensate output data of said flowmeter pertaining to said flowing material.

29. The apparatus of claim 28 wherein said apparatus that generates said second signal comprises:

a first sensor coupled to said flow tube;

circuitry that extends signals from said first sensor to said meter electronics denoting the temperature of said flow tube; and said apparatus that generates said third signal comprises:

additional sensors coupled to said plurality of flowmeter elements exclusive of said flow tube;

a network that extends a signal from the outputs of said additional sensors to said meter electronics denoting the composite temperature of said plurality of elements of said flowmeter; and said meter electronics determines the difference between said flow tube temperature and said composite temperature to determine the thermal stresses applied by said plurality of elements to said flow tube.

30. The apparatus of claim 29 wherein said plurality of elements comprise said balance bar and said case with a first one of said additional sensors being coupled to said case and with at least one of said additional sensors being coupled to said balance bar.

31. The apparatus of claim 30 further comprising circuitry for connecting said additional sensors in series to form said network.

32. The apparatus of claim 31 further including circuitry that connects the output of said network over at least two conductors to said meter electronics.

33. The Coriolis flowmeter of claim 32 wherein said additional sensors comprise:

a second additional sensor and a third additional sensor each coupled to different locations of said balance bar;

a fourth additional sensor coupled to said case;

a first circuit comprising a series connection of the signal outputs of said second and third and fourth additional sensors;

said network extends said series connection of outputs of said second and third and fourth additional sensors to said meter electronics to provide information regarding the composite temperature of the portions of said case and said balance bar to which said second and third and fourth additional sensors are coupled.

34. The Coriolis flowmeter of claim 33 wherein said second additional sensor is proximate an end portion of said balance bar.

35. The Coriolis flowmeter of claim 34 wherein said third additional sensor is coupled to a portion of said balance bar axially inward with respect to said portion of said balance bar to which said second additional sensor is coupled.

36. The Coriolis flowmeter of claim 35 wherein:

said fourth additional sensor is connected to an inner wall of said case.

37. The Coriolis flowmeter of claim 33 wherein:

each of said additional sensors has a first and a second output terminal;

said series connection of said outputs of said second and third and fourth additional sensors connects said first and second output terminals of said second and third and fourth additional sensors in series to said first circuit so that the signals applied to said network represent a composite of the signal outputs of said second and third and fourth additional sensors.

38. The Coriolis flowmeter of claim 37 wherein said network comprises a first circuit that consists of two conductors extending between said series connection of said outputs of said second and third and fourth additional sensors and said meter electronics.

39. The Coriolis flowmeter of claim 38 wherein said network further comprises a second circuit consisting of two conductors extending from a said first sensor coupled to said flow tube to said meter electronics.

40. The Coriolis flowmeter of claim 39 wherein said second circuit that connects said signal output of said first sensor with said signal processing means includes two wires of which one wire is one of said two wires of said first circuit and the other wire of which is unique to said second circuit.

41. The Coriolis flowmeter of claim 40 wherein each of said circuits has a ground terminal connected in common to the ground terminal of each other of said circuits and
a single conductor connects the common ground terminals of each of said sensors with said meter electronics.

42. The Coriolis flowmeter of claim 41 in which three conductors connect said outputs of said circuits with said meter electronics;
a first one of said three conductors being unique to said first circuit;
a second one of said three conductors is unique to said second circuit;
a third one of said three conductors is common to both said first circuit and to said second circuit.

43. The apparatus of claim 28 wherein said meter electronics also derives corrected output data regarding the flow of said material.

44. The apparatus of claim 28 wherein said meter electronics is programmed with instructions for directing a processor in said meter electronics to generate compensated output data by
determining an uncompensated mass flow rate;
deriving a modulus compensation;
deriving a thermal stress compensation; and
using said uncompensated mass flow rate and said modulus compensation and said thermal stress compensation to derive a corrected mass flow rate;
said meter electronics having a memory readable by said processor for storing said instructions.

45. The apparatus of claim 44 characterized in that said corrected mass flow rate is obtained by said instructions multiplying said uncompensated mass flow rate by 1 plus said thermal stress compensation and 1+ said modulus compensation.

46. The apparatus of claim 45 characterized in that said corrected mass flow rate is further obtained by said instructions:
deriving a density compensation;
multiplying said uncompensated mass flow rate by the 1 plus said stress compensation and 1+ said modulus compensation and 1+ said density compensation to obtain a corrected mass flow rate.

47. The apparatus of claim 44 characterized in that said instructions generate said uncompensated flow rate by solving the expression $$FCF \cdot (\Delta t_{meas} - \Delta t_0)$$

Where:
FCF=Flowmeter calibration factor
$\Delta t_{meas}$=Time delay of pick-off signals
$\Delta t_0$=Time delay at zero material flow.

48. The apparatus of claim 44 characterized in that said instructions that derive said modulus compensation solve the expression $$(k_{ft1} \cdot T_f)$$

Where:
$k_{ft1}$=Flowmeter constant based on change in flow tube modulus with temperature
$T_f$=Flow tube temperature.

49. The apparatus of claim 44 characterized in that said instructions that derive said thermal stress compensation solve the expression $$(k_{ft2}(T_f - T_{com}))$$

Where:
$k_{ft2}$=Flowmeter constant based on change in thermal stress with temperature
$T_f$=Flow tube temperature
$T_{com}$=Composite temperature of network sensors.

50. The apparatus of claim 44 characterized in that said instructions that derive said density compensation solve the expression $$k_{ft3} \cdot (\tau_{ct} - k_2)$$

Where:
$k_{ft3}$=Constant for density effect on material flow
$\tau_{ct}$=Temperature and stress compensated tube vibration period
$k_2$=Tube vibration period constant determined at time of density calibration of flowmeter.

51. The apparatus of claim 44 characterized in that said instructions that generate corrected output data derive a corrected mass flow rate by solving the expression:

$$\dot{m} = FCF \cdot (\Delta t_{meas} - \Delta t_0) \cdot [1+(k_{ft1} \cdot T_f)] \cdot [1+k_{ft2}(T_f-T_{com})] \cdot [1+k_{ft3} \cdot (\tau_{ct}-k_2)]$$

Where:
$\dot{m}$=Mass flow rate
FCF=Flow Calibration factor
$\Delta t_{meas}$=Time delay of pick off signals
$\Delta t_0$=Time delay at zero flow
$k_{ft1}$=Meter constant based on change in flow tube modulus with temperature
$k_{ft2}$=Meter constant based on change in thermal stress with temperature
$k_{ft3}$=Meter constant for density effect on flow
$k_2$=Tube vibration period constant determined at time of density calibration of flowmeter
$T_f$=Flow tube temperature
$T_{com}$=Temperature of network sensors
$\tau_{ct}$=Temperature compensated tube vibration period.

52. The apparatus of claim 44 characterized in that said instructions that generate corrected output data derive a corrected mass flow rate by solving the expression:

$$\dot{m} = \dot{m}_{unc}[1+MOD_{comp}] \cdot [1+STRESS_{comp}] \cdot [1+DENSITY_{comp}]$$

Where:
$\dot{m}=FCF(\Delta t_{meas}-\Delta t_0)$
$MOD_{comp}=k_{ft1} \cdot T_1$
$STRESS_{comp}=k_{ft2} \cdot (T_f-T_{com})$
$DENSITY_{comp}=k_{ft3} \cdot (\tau_{CT}-k_2)$
$\dot{m}_{unc}$=the uncompensated mass flow rate
$k_{ft3}$=Meter constant for density effect on flow
$\dot{m}$=Mass flow rate FCF=Flow calibration factor
$\Delta t_{meas}$=Time delay of pick off signals
$\Delta t_0$=Time delay at zero material flow
$k_{ft1}$=Meter constant based on change in flow tube modulus with temperature
$k_{ft2}$=Meter constant based on change in thermal stress with temperature
$T_f$=Flow tube temperature
$T_{com}$=Temperature of network sensors
$\tau_{ct}$=Temperature and stress compensated flow tube vibration period.

53. The apparatus of claim 28 wherein said meter electronics is programmed with instructions for directing a processor in said meter electronics to generate corrected output data regarding the density of said material;
said meter electronics has a memory readable by said processor for storing said instructions.

54. The apparatus of claim 53 wherein said instructions obtain corrected output data regarding density by:
configuring said flowmeter to input constants from memory;
calibrating said flowmeter to derive constants;
determining an uncompensated flow rate;
determining a compensated tube period corrected for flow;
determining a tube period corrected for flow, modulus, and stress;
determining a linear density equation;
determining a differential tube period equal to the difference between said compensated tube period and a flowmeter constant $k_2$ determined during density calibration of said flowmeter;
multiplying said linear density equation by the sum of 1+ the product of a meter constant $c_3$ times the square of said differential tube period+the product of a flowmeter constant $c_4$ times said differential tube period.

55. The apparatus of claim 53 wherein said instructions derive corrected output data regarding density of said material by:
configuring said flowmeter to input constants $a_1, a_2, c_3, c_4$, and $F_d$ from a memory of said meter electronics,
Where:
$F_d$=Density flow effect constant
$a_1\&a_2$=Tube vibration period temperature correction constants for modulus and stress
$c_3\&c_4$=Straight tube material density correction constants.

56. The apparatus of claim 53 wherein said instructions derive corrected output data regarding density of said material by calibrating said flowmeter to determine constants $c_1, c_2, k_2$, and $\Delta t_0$,
Where:
$\Delta t_0$=Time delay at zero flow
$k_2$=Tube vibration period constant determined at time of material density calibration, and
$c_1$ and $c_2$ are constants.

57. The apparatus of claim 53 wherein said instructions derive corrected output data regarding density of said material by executing the steps of:

measuring $\Delta t_{meas}, \Delta t_0$ and $\tau_m$

Where:
$\Delta t_{meas}$=Time delay of pick off signals
$\Delta t_0$=Time delay at zero material flow
$\tau_m$=Raw measured flow tube vibration period.

58. The apparatus of claim 53 wherein said instructions derive corrected output data regarding density of said material by determining $$\dot{m}_{unc}=FCF(\Delta t_{meas}-\Delta t_0)$$

Where:

$\dot{m}_{unc}$ = the uncompensated mass flow rate $FCF$ = Flow Calibration factor $\Delta t_{meas}$ = Time delay of pick-off signals $\Delta t_0$ = Time delay at zero flow.

59. The apparatus of claim 53 wherein said instructions derive corrected output data regarding density of said material by calculating $$\tau_{fd}=\tau_m-\dot{m}^2 \cdot F_d$$

Where:
$\tau_{fd}$=Compensated tube vibration period for mass flow effect
$\tau_m$=Raw measured flow tube vibration period
$\dot{m}$=Mass flow rate
$F_d$=Density flow effect constant.

60. The apparatus of claim 53 wherein said instruction derive corrected output data regarding density of said material by
calculating the expression $$\tau_{cp}=\tau_{fd} \cdot \sqrt{1+a_1 \cdot T_f+a_2 \cdot (T_f-T_{com})}$$

Where:
$T_f$=Flow tube temperature
$T_{com}$=Temperature of network sensors
$\tau_{cp}$=Compensated flow tube vibration period for modulus, stress, and flow
$\tau_{fd}$=Compensated tube vibration period for mass flow effect
$a_1\&a_2$=Tube vibration period temperature correction constants for modulus and stress.

61. The apparatus of claim 53 wherein said instructions derive corrected output data regarding the density of said material by calculating the deviation of the material density from that determined by the linear density equation $$\rho_m=(c_1 \cdot \tau_{cp}^2-c_2)$$

Where:
$\rho_m$=determined material density
$c_1$ and $c_2$ are constants and
$\tau_{cp}^2$ is the compensated period squared.

62. The apparatus of claim 61 wherein said step of deriving corrected output data regarding density of said material includes the step of:
multiplying the expression $$\rho_m=(c_1 \cdot \tau_{cp}^2-c_2)$$

representing linear components by the expression $$(1+c_3 \cdot (\tau_{cp}-k_2)^2+c_4 \cdot (\tau_{cp}-k_2))$$

representing non linear components
Where:
    $\tau_{cp}$=Compensated flow tube vibration period for modulus, stress, and flow
    $\rho_m$=determined material density
    $k_2$=Tube vibration period constant determined at time of material density calibration.
    $c_1,c_2,c_3,\&c_4$=Single tube material density correction constants.

63. The apparatus of claim 53 wherein said instructions derive corrected output data regarding density of said material by calculating the density of said material from the expression $$\rho_m=(c_1 \cdot \tau_{cp}^2-c_2) \cdot (1+c_3 \cdot (\tau_{cp}-k_2)^2+c_4 \cdot (\tau_{cp}-k_2))$$

Where:
    $\rho_{cp}$=Compensated flow tube vibration period for modulus, stress,
    $\rho_m$=determined material density
    $k_2$=Tube vibration period constant determined at time of material density calibration, and
    $c_1,c_2,c_3\& c_4$=Single tube material density correction constants.

64. The apparatus of claim 62 wherein said instructions determine the value $\tau_{cp}$ by solving the expression:

$$\tau_{cp}=\tau_{fd} \cdot \sqrt{1+a_1 \cdot T_f+a_2 \cdot (T_f-T_{com})}$$

Where:
    $T_f$=Flow tube temperature
    $T_{com}$=Temperature of network sensors
    $\tau_{cp}$=Compensated flow tube vibration period for modulus, stress, and flow
    $\tau_{fd}$=Compensated tube vibration period for mass flow effect
    $a_1 \cdot T_f$=the modulus effect on density effect
    $a_2 \cdot (T_f-T_{com})$=the thermal stress effect on density
    $a_1$ and $a_2$=are flowmeter constants pertaining to density.

65. The apparatus of claim 53 wherein said instructions generate corrected output data regarding said density by solving the expression;

$$\rho_m=(\text{Density}_{linear})[1+c_3(\Delta\text{Period}_{comp})^2+c_4(\Delta\text{Period}_{comp})]$$

Where:
    $\text{Density}_{linear}=\rho_m=c_1 \cdot \tau_{cp}^2-c_2$
    The term $(\Delta\text{Period}_{comp})$ is the difference between the compensated tube period $\tau_{cp}$(for temperature, stress, and flow) and a tube period constant $k_2$ determined during density calibration,
    Where:
        $\tau_{cp}$=Compensated flow tube vibration period for modulus, stress, and flow
        $c_3,\&c_4$=Single tube material density correction constants,
        $c_1$ and $c_2$ are constants and
        $\rho_m$=determined material density.

66. The apparatus of claim 53 wherein said instructions that obtain corrected output data regarding density includes instructions for:
    determining a compensated tube period;
    determining a linear density equation;
    determining a differential tube period equal to the difference between said compensated tube period and a flowmeter constant $k_2$ determined during density calibration of said flowmeter;
    multiplying said linear density equation by the sum of 1+ the product of a meter constant $c_3$ times the square of said differential tube period+the product of a flowmeter constant $c_4$ times said differential tube period.

67. The apparatus of claim 66 wherein said instructions determine the value of $\tau_{cp}$ by solving the expression:

$$\tau_{cp}=\tau_{fd} \cdot \sqrt{1+a_1 \cdot T_f+a_2 \cdot (T_f-T_{com})}$$

Where:
    $\tau_{cp}$=Compensated flow tube vibration period for modulus, stress, and flow
    $\tau_{fd}$=Compensated tube vibration period for mass flow effect
    $T_f$=Flow tube temperature
    $T_{com}$=Temperature of network sensors
    $a_1 \cdot T_f$=the modulus thermal density effect
    $T_f-T_{com}$=the thermal stress effect on density
    $a_1$ and $a_2$=are flowmeter constants pertaining to density.

68. A method of operating a Coriolis flowmeter to determine the density of a material flow in said Coriolis flowmeter: said method comprising the steps of:
    configuring said Coriolis flowmeter from information stored in a memory of said Coriolis flowmeter to determine configured meter parameters;
    calibrate said Coriolis flowmeter for density of said flowing material using a two point linear calibration method employing two different materials of different density to derive calibration parameters for a linear density equation;
    determine a measured flow tube vibration period from signals received from pick-off sensors coupled to said flow tube of said Coriolis flowmeter;
    measuring operational parameters of said Coriolis flowmeter;
    determine a compensated flow tube vibration period using said measured flow tube vibration period and said operational parameters and said configured meter parameters;
    determining a non-linear component using said compensated flow tube vibration period and said configured meter parameters and said calibration parameters;
    obtaining a non-linear density equation for said Coriolis flowmeter by combining said linear density equation with said non-linear component to yield a single flow tube density equation which specifies the deviation of said Coriolis flowmeter calibration from linear; and
    determining the density of said material using said single flow tube density equation and said compensated tube period.

69. The method of claim 68 wherein said step of configuring said Coriolis flowmeter includes the step of determining parameters $a_1,a_2,c_3,c_4$, and $F_d$,
    Where:
        $a_1$ and $a_2$ are flowmeter constants pertaining to modulus and thermal stress effect on density
        $C_3,\&c_4$=Single tube material density correction constants, and
        $F_d$=Density flow effect constant.

70. The method of claim 68 wherein said step of calibrating includes the step of using two flowing materials comprising air and water.

71. The method of claim 68 wherein said step of calibrating includes the step of deriving the linear density equation $$\rho_m=(c_1\tau_{cp}^2-c_2)$$

Where:
- $c_1$ and $c_2$ are constants and
- $\tau_{cp}^2$ is the compensated period squared, and
- $\rho_m$=determined material density.

72. The method of claim 68 wherein said step of measuring includes the step of measuring the flow tube vibration period, the time delay at zero flow, the time delay with flow, the temperature of the flow tube, and the composite temperature of the flow meter while said Coriolis flowmeter contains said flowing material of unknown density.

73. The method of claim 68 wherein said step of determining a compensated flow tube vibration period for mass flow includes the step of solving the equation $$\tau_{fd} = \tau m - \dot{m} F_d.$$

74. The method of claim 68 wherein said step of determining a compensated flow tube vibration period includes the step of determining said flow tube vibration period compensated for flow, modulus, and stress using the equation $$\tau_{cp} = \tau_{fd} \sqrt{1 + a_1 T_f + a_2 \cdot (T_f - T_{com})}$$

Where:
- $\tau_{fd}$=Compensated tube vibration period for mass flow effect
- $\tau_{cp}$=Compensated flow tube vibration period for modulus, stress, and flow
- $a_1 \cdot T_f$=the modulus effect on density,
- $T_f$=Flow tube temperature
- $T_{com}$=Temperature of network sensors
- $a_2(T_f - T_{com})$=the thermal stress effect on density, and
- $a_2$ and $a_2$ are flowmeter constants pertaining to modulus and thermal stress effect on density.

75. The method of claim 68 wherein step of determining a non-linear component includes the step of evaluating the expression $$(1 + c_3(\tau_{cp} - k_2)^2 + c_4 \cdot (\tau_{cp} - k_2))$$

Where:
- $\tau_{cp}$=Compensated flow tube vibration period for modulus, stress, and flow
- $k_2$=Tube vibration period constant determined at time of material density calibration.
- $c_3$,& $c_4$=Single tube material density correction constants.

\* \* \* \* \*

UNITED STATES PATENT AND TRADEMARK OFFICE
CERTIFICATE OF CORRECTION

PATENT NO. : 6,327,915 B1
DATED : December 11, 2001
INVENTOR(S) : Craig Brainerd Van Cleve, Charles Paul Stack and Gregory Treat Lanham It is certified that error appears in the above-identified patent and that said Letters Patent is hereby corrected as shown below:

Column 7,
Line 54,
  replace "$T_{f2}$ = Flow Tube Temperature"
  with -- $T_f$ = Flow Tube Temperature --

Line 62,
  replace "$\tau_{f3}$ = Meter constant for density effect on flow"
  with -- $k_{f3}$ = Meter constant for density effect on flow --

Column 10,
Line 61, replace "following description thereof together with thee drawings in"
with -- following description thereof together with the drawings in --

Column 15,
Line 10,
  replace "$a_1$ & $a_2$ = Density temperature correction constants It will be"
  with -- $a_1$ & $a_2$ = Density temperature correction constants
         It will be noted that equation 5 contains under the radical of term--

Column 20,
Line 32,
  replace "rial density $\rho_m$. The material density $\tau_m$ is the transmitted via"
  with -- rial density $\rho_m$. The material density $\rho_m$ is the transmitted via --

Column 22,
Line 36,
  replace "$k_{f3} \cdot (\tau_{ct} k_2)$"
  with -- $k_{f3} \cdot (\tau_{ct} - k_2)$ --

Line 55,
  replace "$\Delta t_0$ = Time delay at zero flow"
  with -- $\Delta t_0$ = Time delay at zero material flow --

UNITED STATES PATENT AND TRADEMARK OFFICE
CERTIFICATE OF CORRECTION

PATENT NO.      : 6,327,915 B1
DATED           : December 11, 2001
INVENTOR(S)     : Craig Brainerd Van Cleve, Charles Paul Stack and Gregory Treat Lanham It is certified that error appears in the above-identified patent and that said Letters Patent is hereby corrected as shown below:

<u>Column 22, cont'd,</u>
Line 60, replace "$k_{f3}$ = Meter constant for density effect on flow"

with -- $k_{f3}$ = Constant for density effect on flow --

<u>Column 24,</u>
Line 16, replace "calculating $\tau_{fd1} = \tau_m - \dot{m}^2 \cdot F_d$"

with -- calculating $\tau_{fd} = \tau_m - \dot{m}^2 \cdot F_d$ --

<u>Column 28,</u>
Line 43, replace "$\Delta t_0$ = Time delay at zero flow"

with -- $\Delta t_0$ = Time delay at zero material flow --

Line 48, replace "$k_{f3}$ = Meter constant for density effect on flow"

with -- $k_{f3}$ = Meter constant for density effect on material flow --

Line 53, replace "$\tau_{ct}$ = Temperature compensated tube vibration period"

with -- $\tau_{ct}$ = Temperature and stress compensated flow tube vibration period --

Line 61, replace "$\dot{m} = FCF(\Delta t_{meas} - \Delta t_0)$"

with -- $\dot{m}_{unc} = FCF(\Delta t_{meas} - \Delta t_0)$ --

UNITED STATES PATENT AND TRADEMARK OFFICE
CERTIFICATE OF CORRECTION

PATENT NO. : 6,327,915 B1
DATED : December 11, 2001
INVENTOR(S) : Craig Brainerd Van Cleve, Charles Paul Stack and Gregory Treat Lanham It is certified that error appears in the above-identified patent and that said Letters Patent is hereby corrected as shown below:

Column 28 cont'd,
Line 66, replace "$k_{f13}$ =Meter constant for density effect on flow"

with -- $k_{f13}$ =Meter constant for density effect on material flow --

Column 31,
Line 18, replace "$\rho_{cp}$ = Compensated flow tube vibration period for modulus, stress,"

with -- $\tau_{cp}$ = Compensated flow tube vibration period for modulus, stress, --

Column 33,
Line 15, replace "$\tau_{fd} = \tau m - m F_d \cdot$"

with -- $\tau_{fd} = \tau_m - \overset{2}{m} \cdot F_d$ --

Line 17,

Insert: Where:

$\tau_{fd}$ = Compensated tube vibration period for mass flow effect $\tau_m$ = Raw measured flow tube vibration period $\dot{m}$ = Mass flow rate $F_d$ = Density flow effect constant Line 23, replace "$\tau_{cp} = \tau_{fd} \sqrt{1 + a_1 T_f + a_2 \cdot (T_f} - T_{com})$"

with -- $\tau_{cp} = \tau_{fd} \sqrt{1 + a_1 T_f + a_2 (T_f} - T_{com})$ --

UNITED STATES PATENT AND TRADEMARK OFFICE
CERTIFICATE OF CORRECTION

PATENT NO.    : 6,327,915 B1
DATED         : December 11, 2001
INVENTOR(S)   : Craig Brainerd Van Cleve, Charles Paul Stack and Gregory Treat Lanham It is certified that error appears in the above-identified patent and that said Letters Patent is hereby corrected as shown below:

Column 34,
Line 10, replace "$a_2$ and $a_2$ are flowmeter constants pertaining to modulus"

with -- $a_1$ and $a_2$ are flowmeter constants pertaining to modulus --

Line 15, replace "$(1 + c_3(\tau_{cp} - k_2)^2 + c_4 \cdot (\tau_{cp} - k_2))$"

with -- $(1 + c_3 \cdot (\tau_{cp} - k_2)^2 + c_4 \cdot (\tau_{cp} - k_2))$ --

Signed and Sealed this

Twenty-fifth Day of February, 2003

JAMES E. ROGAN
*Director of the United States Patent and Trademark Office*